us011267890B2

(12) United States Patent
Wu et al.

(10) Patent No.: US 11,267,890 B2
(45) Date of Patent: Mar. 8, 2022

(54) ANTI-PD-L1 ANTIBODY AND APPLICATION THEREOF

(71) Applicants: SHANGHAI JUNSHI BIOSCIENCES CO., LTD., Shanghai (CN); SUZHOU JUNMENG BIOSCIENCES CO., LTD., Jiangsu (CN)

(72) Inventors: Hai Wu, Shanghai (CN); Sheng Yao, Shanghai (CN); Yuehua Zhou, Jiangsu (CN); Jian Yao, Shanghai (CN); Dan Meng, Jiangsu (CN); Hui Feng, Shanghai (CN)

(73) Assignees: SHANGHAI JUNSHI BIOSCIENCES INC., Shanghai (CN); SUZHOU JUNMENG BIOSCIENCES CO., LTD., Jiangsu (CN)

( * ) Notice: Subject to any disclaimer, the term of this patent is extended or adjusted under 35 U.S.C. 154(b) by 104 days.

(21) Appl. No.: 16/487,035

(22) PCT Filed: Feb. 13, 2018

(86) PCT No.: PCT/CN2018/076669
§ 371 (c)(1),
(2) Date: Aug. 19, 2019

(87) PCT Pub. No.: WO2018/153320
PCT Pub. Date: Aug. 30, 2018

(65) Prior Publication Data
US 2019/0367618 A1 Dec. 5, 2019

(30) Foreign Application Priority Data
Feb. 13, 2018 (CN) .......................... 201710093631.6

(51) Int. Cl.
A61K 39/395 (2006.01)
C07K 16/00 (2006.01)
C07K 16/46 (2006.01)
C07H 21/04 (2006.01)
C12P 21/06 (2006.01)
C12N 1/20 (2006.01)
C12N 15/74 (2006.01)
C07K 16/28 (2006.01)
A61P 35/00 (2006.01)

(52) U.S. Cl.
CPC .......... C07K 16/2827 (2013.01); A61P 35/00 (2018.01); C07K 2317/24 (2013.01); C07K 2317/565 (2013.01); C07K 2317/92 (2013.01)

(58) Field of Classification Search
None
See application file for complete search history.

(56) References Cited

U.S. PATENT DOCUMENTS 10,000,564 B2 * 6/2018 Murphy .................. A61P 25/00
10,161,930 B2 * 12/2018 Beau-Larvor .......... C07K 16/30

FOREIGN PATENT DOCUMENTS

| CN | 103987405 A | 8/2014 | |
| CN | 104479018 A | 4/2015 | |
| CN | 104736168 A | 6/2015 | |
| CN | 105669864 A | 6/2016 | |
| CN | 105968200 A | 9/2016 | |
| CN | 106065031 A | 11/2016 | |
| CN | 106397592 A | 2/2017 | |
| WO | 2007/005874 A2 | 1/2007 | |
| WO | 2007/005874 A3 | 1/2007 | |
| WO | 2010/077634 A1 | 7/2010 | |
| WO | 2011/066389 A1 | 6/2011 | |
| WO | 2013/079174 A1 | 6/2013 | |
| WO | WO-2016022630 A1 * | 2/2016 | .............. A61P 31/10 |

OTHER PUBLICATIONS

Brown et al. Tolerance of single, but not multiple, amino acid replacements in antibody VH CDR2: a means of minimizing B cell wastage from somatic hypermutation? J. Immuno. May 1996, 3285-91. (Year: 1996).*
Vajdos et al. Comprehensive functional maps of the antigen-binding site of an anti-ErbB2 antibody obtained with shotgun scanning mutagenesis. J. Mol. Biol. Jul. 5, 2002, 320(2):415-28. (Year: 2002).*
Xu-Monette et al. PD-1/PD-L1 Blockade: Have We Found the Key to Unleash the Antitumor Immune Response? Front. Immunol. 8: 1597, pp. 1-29. (Year: 2017).*
International Search Report in PCT/CN2018/076669, dated Apr. 28, 2018.
Liu, et al. "Structural basis of anti-PD-L1 monoclonal antibody avelumab for tumor therapy." Cell research 27, No. 1 (2017): 151.
Pini, et al. "Design and use of a phage display library Human antibodies with subnanomolar affinity against a marker of angiogenesis eluted from a two-dimensional gel." Journal of Biological Chemistry 273, No. 34 (1998): 21769-21776.

(Continued)

Primary Examiner — Maher M Haddad
(74) Attorney, Agent, or Firm — Kilpatrick Townsend & Stockton LLP

(57) ABSTRACT

An antibody or a functional fragment thereof that specifically bind to PD-L1 with high affinity, a nucleic acid molecule that encodes said antibody or the functional fragment thereof, an expression vector and a host cell for use in expressing said antibody or the functional fragment thereof, and a method for producing said antibody or the functional fragment thereof. An immunoconjugate and a pharmaceutical composition containing said antibody or the functional fragment thereof, and a method for using said antibody or the functional fragment thereof to enhance the function of a T cell so as to up-regulate a cell-mediated immune response, for use in treating diseases caused by T cell dysfunction.

17 Claims, 16 Drawing Sheets

Specification includes a Sequence Listing.

(56) References Cited

OTHER PUBLICATIONS

Chen et al., "Anti-PD-1/PD-L1 therapy of human cancer: past, present, and future", The Journal of Clinical Investigation, vol. 125, No. 9, Sep. 2015, pp. 3384-3391.
EP18757365.4, "Extended European Search Report", Jun. 7, 2021, 17 pages.

* cited by examiner

FACS detection of the effect of candidate hybridoma cells in inhibiting the binding of PD-L1 to PD-1

ANTI-PD-L1 ANTIBODY AND APPLICATION THEREOF

CROSS REFERENCE TO RELATED APPLICATIONS

This application is a U.S. National Stage of PCT/CN2018/076669, international filing date Feb. 13, 2018, the disclosure of which are incorporated herein by reference.

REFERENCE TO SUBMISSION OF A SEQUENCE LISTING AS A TEXT FILE

The Sequence Listing written in file SEQ_088448-1152677.txt created on Aug. 15, 2019, 28,672 bytes, machine format IBM-PC, MS-Windows operating system, is hereby incorporated by reference in its entirety for all purposes.

TECHNICAL FIELD

The disclosure is in the field of biomedicine. The disclosure provides antigenic polypeptides, which can be used to produce antibodies capable of binding to PD-L1-derived molecules. The disclosure also relates to an antibody or a functional fragment thereof which specifically binds to PD-L1 with high affinity. The disclosure further provides nucleic acid molecules encoding the antibodies described herein or functional fragments thereof, expression vectors and host cells for expressing the antibodies or functional fragments thereof, and methods of producing the antibodies or functional fragments thereof. The disclosure further provides immuno-conjugates and pharmaceutical compositions comprising an antibody described herein or a functional fragment thereof, and a method of up-regulating a cell-mediated immune response by using the antibody or a functional fragment thereof to enhance the function of a T cell, for use in the treatment of T cell dysfunction diseases.

BACKGROUND ART

Programmed death-ligand 1 (PD-L1), also known as cluster of differentiation 274 (CD274) or B7 homolog 1 (B7-H1), is a type I transmembrane glycoprotein consisting of 290 amino acid residues, comprising an IgV-like region, an IgC-like region, a transmembrane hydrophobic region, and a 30-amino acid intracellular tail, the molecular weight of which is 40 kDa as a complete molecule. PD-L1 mRNA is expressed in almost all tissues, but sustained expression of PD-L1 protein is only found in a small number of tissues, including liver, lung, tonsil, and immuno-privileged tissues such as the eye and placenta. PD-L1 is also expressed in activated T cells, B cells, monocytes, dendritic cells, macrophages, and the like.

The receptor for PD-L1 is PD-1, which is mainly expressed on the surface of immune cells such as $CD4^+$ T cells, $CD8^+$ T cells, NK T cells, B cells, and activated monocytes. The binding of PD-L1 to PD-1 can initiate the phosphorylation of the tyrosine residue of ITIM (Immunoreceptor Tyrosine Inhibition Module) in the cytoplasmic region of PD-1, which promotes the binding of tyrosine phospholipase to SHP2 and activate SHP2, in turn causes the dephosphorylation of the downstream Syk and PI3K to deliver a termination signal, which limits the interaction of antigen presenting cells or dendritic cells with T cells. The binding can further inhibit the metabolism of T cells, inhibit the secretion of anti-apoptotic protein Bcl-X2, reduce the secretion of effector cytokines IL-2 and IFN-γ, induce T cell depletion and apoptosis, thereby reducing immune responses in which T cells is involved, and exerting a negative regulatory function.

T cells recognize the antigen and secrete IFN-γ after activation. T cell-derived IFN-γ augments and maintains T cell functions, such as up-regulating MHC molecules, enhancing antigen processing and presentation of the target cells, and promoting T cell differentiation. IFN-γ also induces PD-L1 expression in tissues of the immune inflammation site, preventing excessive immunity from harming tissues. IFN-γ can induce the expression of PD-L1 on the surface of normal epithelial cells, vascular endothelial cells, myeloid cells, naive T cells and the like. IFN-γ-induced interferon regulatory factor 1 (IRF-1) can also bind to the interferon regulatory factor binding site located at 200 bp and 320 bp upstream of the PD-L1 transcription initiation site to regulate PD-L1 from the transcriptional level. PD-L1 can bind to PD-1 on the surface of T cells to exert a negative regulatory function, so that the inflammatory site is protected.

The negative regulatory function of PD-L1 plays an important role in tumor immunity. In 2004, Konishi et al. first discovered the expression of PD-L1 in tissue samples from patients with non-small cell lung cancer. Subsequently, PD-L1 was found to be expressed in tissues of patients with various tumor, including gastric cancer, lung cancer, liver cancer, intrahepatic cholangiocarcinoma, colon cancer, pancreatic cancer, ovarian cancer, breast cancer, cervical cancer, head and neck squamous cell carcinoma, nasopharyngeal cancer, esophageal cancer, bladder cancer, renal cell carcinoma, skin cancer, oral squamous cell carcinoma, etc. During cell canceration, new protein molecules are produced due to gene mutations, foreign gene (viral) expression or quiescent gene activation. After these proteins are degraded in cells, some degraded peptide fragments can be expressed on the cell surface, becoming tumor antigens. The immune system can identify tumor antigens and eliminate tumor cells through immune surveillance, while tumor cells use PD-L1 to evade immune attacks.

Expression of PD-L1 at the tumor site can protect tumor cells from injury through a variety of ways. Tumor-infiltrating lymphocytes (TILs) secrete IFN-γ to induce expression of PD-L1 by tumor cells and surrounding stromal cells. The PD-L1 of tumor cells can bind to PD-1 on TILs, inhibiting the activation of TIL cells, and further causing the apoptosis of TIL cells. In vitro experiments have shown that tumor cell-associated PD-L1 can increase the apoptosis of tumor-specific T cells, while PD-L1 monoclonal antibodies can attenuate this effect. Tumor-associated PD-L1 can promote T cell expression of IL-10, further inhibiting the immune response. PD-L1 is not only a ligand for PD-1, but it can also act as a receptor to transmit a reverse signal to protect tumor cells from apoptosis induced by other anti-tumor pathways, such as FAS-FASL.

A variety of chronic and acute viruses also use PD-L1 signals to evade human immunodetection. Wang et al. found that the expression of PD-L1 was up-regulated in bone marrow-derived dendritic cells from HIV-infected patients. After anti-virus infection and inhibition of HIV replication, PD-L1 expression was down-regulated, accompanied by up-regulation of T cell numbers; according to Chen et al., the expression of PD-L1 on T lymphocytes and dendritic cells in chronic HBV-infected patients was also found to be up-regulated. Viral infection induces high expression of PD-L1 in infected cells, and induces CD8⁺ T cells to express PD-1, thereby inhibiting T cell action, resulting in the depletion of effector T cells.

SUMMARY

It is an object herein to provide an antibody which enhances the relevant target of T cell function and a functional fragment of said antibody, and a method for treating T cell dysfunction diseases by using said antibody or the functional fragment of the antibody to enhance the function of T cells to upregulate a cell-mediated immune response.

In order to achieve the above object, intensive studies have been conducted and antibodies and functional fragments thereof have been found which specifically bind to PD-L1 and inhibit PD-L1 binding to PD-1, thereby enhancing T cell function. The disclosure includes the following contents.

In one aspect, the antibody or a functional fragment thereof of the disclosure comprises heavy chain CDR(s) selected from the group consisting of amino acid sequences of SEQ ID NOs: 7, 8, 9, 13, 14, 15, 19, 20, 21, 22, 23, 24, 28, 29, 30, or a variant of any of said sequence, and/or light chain CDR(s) selected from the group consisting of amino acid sequences of SEQ ID NOs: 1, 2, 3, 4, 5, 6, 10, 11, 12, 16, 17, 18, 25, 26, 27 or a variant of any of said sequences.

In another aspect, provided herein is an antibody or a functional fragment thereof capable of binding to PD-L1, wherein the amino acid sequences of CDR1, CDR2 and CDR3 of the heavy chain CDRs are selected from one of the following groups of the respective amino acid sequences or variants thereof:

| Group | HCDR1 | HCDR2 | HCDR3 |
|---|---|---|---|
| A | SEQ ID NO: 7 | SEQ ID NO: 8 | SEQ ID NO: 9 |
| B | SEQ ID NO: 13 | SEQ ID NO: 14 | SEQ ID NO: 15 |
| C | SEQ ID NO: 19 | SEQ ID NO: 20 | SEQ ID NO: 21 |
| D | SEQ ID NO: 22 | SEQ ID NO: 23 | SEQ ID NO: 24 |
| E | SEQ ID NO: 28 | SEQ ID NO: 29 | SEQ ID NO: 30 | and/or the amino acid sequences of CDR1, CDR2 and CDR3 of the light chain CDRs are selected from one of the following groups of amino acid sequences or variants thereof:

| Group | LCDR1 | LCDR2 | LCDR3 |
|---|---|---|---|
| F | SEQ ID NO: 1 | SEQ ID NO: 2 | SEQ ID NO: 3 |
| G | SEQ ID NO: 4 | SEQ ID NO: 5 | SEQ ID NO: 6 |
| H | SEQ ID NO: 10 | SEQ ID NO: 11 | SEQ ID NO: 12 |
| I | SEQ ID NO: 16 | SEQ ID NO: 17 | SEQ ID NO: 18 |
| J | SEQ ID NO: 25 | SEQ ID NO: 26 | SEQ ID NO: 27 |

In another aspect, also provided herein is an antibody or a functional fragment thereof capable of binding to PD-L1, wherein the amino acid sequences of the heavy chain CDR1, CDR2 and CDR3 and the light chain CDR1, CDR2 and CDR3 are selected from one of the following groups of amino acid sequences or variants thereof:

| GROUP | LCDR1 | LCDR2 | LCDR3 | HCDR1 | HCDR2 | HCDR3 |
|---|---|---|---|---|---|---|
| 1 | SEQ ID NO: 1 | SEQ ID NO: 2 | SEQ ID NO: 3 | SEQ ID NO: 7 | SEQ ID NO: 8 | SEQ ID NO: 9 |
| 2 | SEQ ID NO: 4 | SEQ ID NO: 5 | SEQ ID NO: 6 | SEQ ID NO: 7 | SEQ ID NO: 8 | SEQ ID NO: 9 |
| 3 | SEQ ID NO: 10 | SEQ ID NO: 11 | SEQ ID NO: 12 | SEQ ID NO: 13 | SEQ ID NO: 14 | SEQ ID NO: 15 |
| 4 | SEQ ID NO: 16 | SEQ ID NO: 17 | SEQ ID NO: 18 | SEQ ID NO: 19 | SEQ ID NO: 20 | SEQ ID NO: 21 |
| 5 | SEQ ID NO: 16 | SEQ ID NO: 17 | SEQ ID NO: 18 | SEQ ID NO: 22 | SEQ ID NO: 23 | SEQ ID NO: 24 |
| 6 | SEQ ID NO: 25 | SEQ ID NO: 26 | SEQ ID NO: 27 | SEQ ID NO: 28 | SEQ ID NO: 29 | SEQ ID NO: 30 |

In another aspect, also provided herein is an antibody or a functional fragment thereof, which is capable of binding to PD-L1, comprising a heavy chain variable region having an amino acid sequence selected from the group consisting of SEQ ID NOs: 33, 35, 37, 38, 40 or any variants thereof, and/or a light chain variable region having an amino acid sequence selected from the group consisting of SEQ ID NOs: 31, 32, 34, 36, 39 or any variants thereof.

In another aspect, also provided herein is an antibody or a functional fragment thereof capable of binding to PD-L1, which is a chimeric antibody, a humanized antibody or a fully human antibody.

In another aspect, also provided herein is nucleic acid molecules encoding the CDRs, light chain variable regions or heavy chain variable regions of the disclosure and complementary sequences thereof, including but not limited to nucleic acid molecules encoding the amino acid sequences set forth in SEQ ID NOs: 1-40, 42, 44, 46, and 48; and expression vectors and host cells comprising the nucleic acid molecules or the complementary sequences thereof.

In another aspect, also provided herein is an isolated nucleic acid molecule encoding a PD-L1 binding antibody or a functional fragment thereof described herein, and a complementary sequence thereof, and an expression vector and a host cell comprising the nucleic acid molecule or its complementary sequence.

In another aspect, also provided is use of an antibody or a functional fragment thereof capable of binding to PD-L1, or a nucleic acid molecule encoding the same, or an expression vector or host cell in the manufacture of a medicament for the enhancement of T cell function so as to up-regulating cell-mediated immune response, or in the manufacture of a medicament for the treatment of a disorder of T cell dysfunction, such as a tumor, an inflammatory disease or the like.

In another aspect, provided herein is a pharmaceutical composition comprising: the PD-L1 binding antibody or a functional fragment thereof described herein, an isolated nucleic acid molecule which encodes the PD-L1 binding antibody or a functional fragment thereof described herein, or an expression vector or host cell that comprises the nucleic acid, or any combination thereof; and a pharmaceutically acceptable carrier.

In another aspect, provided herein is an immunoconjugate comprising an antibody capable of binding to PD-L1 described herein, or a functional fragment thereof, conjugated to a therapeutic agent; preferably the therapeutic agent is a toxin, a radioisotope, a drug or a cytotoxic agent.

DETAILED DESCRIPTION

Figure 1A:
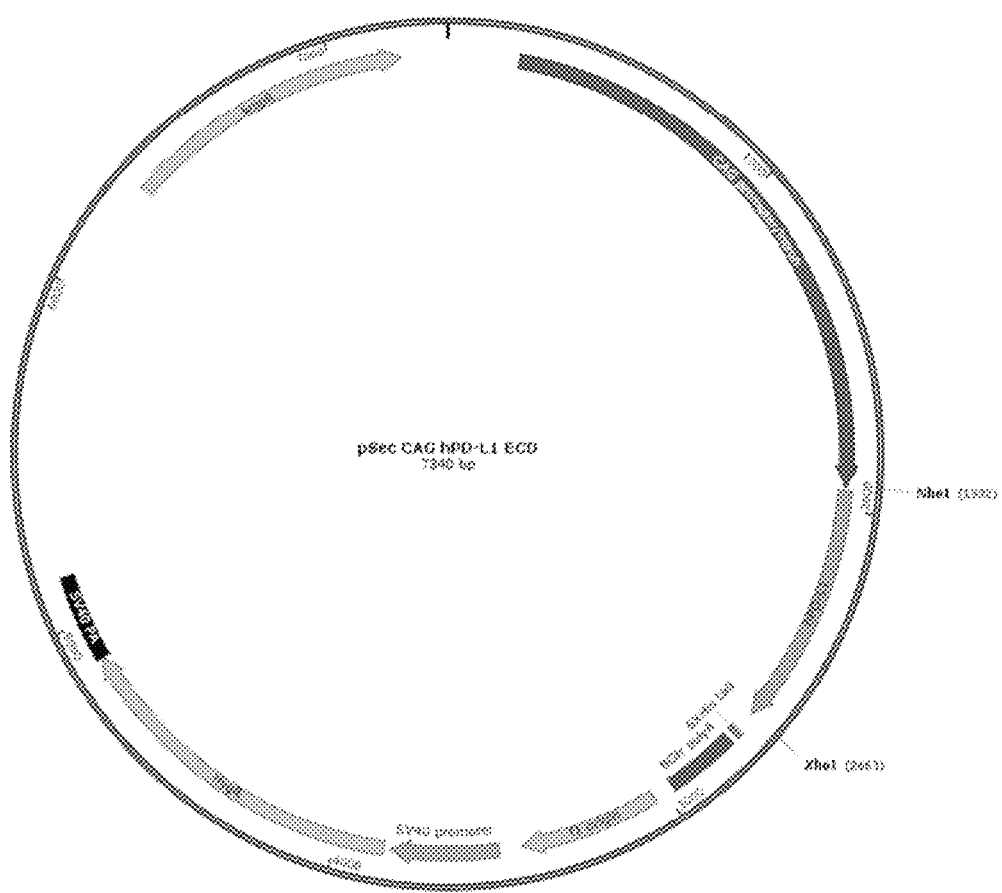
FIG. 1A: Process of pCDNA3.1 plasmid modification to obtain the pSec CAGA2 ECD.

All references mentioned herein are expressly incorporated herein by reference.

General Technology

The practice described herein will employ, unless otherwise defined, conventional techniques of molecular biology (including recombinant techniques), microbiology, cell biology, biochemistry, and immunology, which are within the skills of the art. These techniques are fully explained in the literature, such as Molecular Cloning: A Laboratory Manual, Second Edition (Sambrook et al., 1989); Oligonucleotide Synthesis (M J Gait, ed., 1984); Animal Cell Culture (RI Freshney, ed., 1987); Methods in Enzymology (Academic Press, Inc.); Current Protocols in Molecular Biology) (F. M. Ausubel et al., eds. 1987, and regularly updated versions); PCR: The Polymerase Chain Reaction (Mullis et al., ed., 1994); A Practical Guide to Molecular Cloning (Perbal Bernard V., 1988); Phage Display: A Laboratory Manual (Barbas et al., 2001).

I. Host Immunity 1.1 Lymphocyte Development and Activation

The two main types of lymphocytes in humans are T (thymus derived) and B (bone marrow derived) cells. These cells are derived from hematopoietic stem cells that have been directed to the lymphatic developmental pathway in the bone marrow and fetal liver. The progeny of these stem cells mature into B or T lymphocytes along different pathways. The development of B lymphocytes in humans is completely carried out in the bone marrow. On the other hand, T cells develop from immature precursors that leave the bone marrow and move through the bloodstream to the thymus, where they proliferate and differentiate into mature T lymphocytes.

Mature lymphocytes presented in the thymus or bone marrow are in a quiescent or "resting" state, i.e. they are mitotically inactive. When dispersed into the bloodstream, these "naive" or "virgin" lymphocytes move to a variety of secondary or peripheral lymphoid organs, such as the spleen, lymph nodes, or tonsils. Most virgin lymphocytes have an inherently short life span and die some days after leaving the bone marrow or thymus. However, if such cells receive a signal indicative of the presence of an antigen, they can be activated and undergo successive rounds of cell division. Some of the resulting progeny cells then return to a resting state to become memory lymphocytes—B and T cells, which are substantially sensitized when encounter the stimulating allergen again. The other progeny of the activated virgin lymphocytes are effector cells that survive only for some days but perform specific defense activities.

Lymphocyte activation refers to an ordered series of events through which resting lymphocytes (upon stimulation) undergo division and produce progeny, some of which become effector cells. Complete responses include induction of cell proliferation (mitosis) and expression of immune function. Lymphocytes are activated when receptors on their surface are bound by specific ligands. Such ligands are different for T cells and B cells, but the intracellular physiological mechanisms caused thereby are similar.

Some heterologous antigens themselves can induce lymphocyte activation, particularly large polymeric antigens that cross-link with surface immunoglobulins on B cells or other glycoproteins on T cells. However, most of the antigens are not polymerized, and even they bind to B cells in a large amount does not result in activation. These more commonly presented antigens activate B cells when co-stimulated with adjacent activated helper T-lymphocytes. Such stimulation can result from lymphokines secreted by T cells, but the most efficient delivery is by direct contact of B cells with T cell surface proteins, which interact with certain B cell surface receptors to produce a secondary signal.

1.2 T Cells

T lymphocytes do not express immunoglobulins, but detect the presence of heterologous substances through surface proteins called T cell receptors (TCRs). These receptors recognize antigens by direct contact or by affecting the activity of other immune cells. Together with macrophages, T cells are the major cell type involved in cell-mediated immunity.

Unlike B cells, T cells are capable of detecting heterologous substances only in specific environments. Particularly, T lymphocytes will recognize the heterologous protein only when the heterologous protein is first cleaved into small peptides that are then displayed on the surface of a second host cell, termed as antigen presenting cell (APC). Many types of host cells are capable of presenting antigens under certain conditions, but certain types are more specifically suitable for this purpose and are particularly important in controlling T cell activity, including macrophages and other B cells. The antigen presenting moiety is dependent on a specific protein, the major histocompatibility complex (MHC) protein, which is on the surface of the presenting cell. Therefore, in order to stimulate cell-mediated immunity, the heterologous peptide must be presented in combination with the MHC peptide to the T cell, and this combination must be recognized by the T cell receptor.

There are two major T cell subtypes, cytotoxic T lymphocytes (Tc cells or CTLs) and helper T (TH) cells, which can be roughly identified based on the expression of the markers CD8 and CD4 on the cell surface. Tc cells are important in viral defense and can kill viruses directly by recognizing viral peptides expressed on the surface of certain cells. TH cells promote the proliferation, maturation, and immune function of other cell types, such as lymphokine secretion, thereby controlling the activity of B cells, macrophages, and cytotoxic T cells. Virgin and memory T lymphocytes are usually in a resting state, in which they do not show significant auxiliary or cytotoxic activity. When activated, these cells undergo several rounds of mitosis to produce progeny cells. Some of these progeny cells return to a resting state as memory cells, while others become effector cells, actively expressing auxiliary or cytotoxic activity. These progeny cells are similar to their parents: CD4+ cells produce only CD4+ progeny, while CD8+ cells produce only CD8+ progeny. Effector T cells express cell surface markers that are not expressed on resting T cells, such as CD25, CD28, CD29, CD40L, transferrin receptor, and class II MHC proteins. When activation stimulation is withdrawn, cytotoxic or auxiliary activity gradually degrades over the course of several days as the effector cells die or return to rest.

Similar to the activation of B cells, the response of T lymphocytes to most antigens also requires two types of simultaneous stimulations. The first is an antigen which, if properly displayed by an MHC protein in an antigen presenting cell, is recognized and bound by a T cell receptor. Although this antigen-MHC complex does send signals into cells, it is usually not sufficient to cause T cell activation. Complete activation, such as occurs in helper T cells, requires co-stimulation with other specific ligands (called co-stimulatory factors) expressed on the surface of antigen presenting cells. On the other hand, activation of cytotoxic T cells typically requires IL-2, which is a cytokine secreted by activated helper T cells.

1.3 Immune Response

The three main functional properties of the mammalian immune system that distinguish it from other body defenses include: (1) specificity—the ability to uniquely recognize from and to respond to or not respond to a large number of target molecules, (2) recognition—the ability to distinct self from non-self and to coexist peacefully with all the numerous proteins and other organic molecules, but still react strongly to the heterologous substances introduced into the body, and (3) memory—the ability of empirical modeling, to produce a faster and stronger response upon subsequent encounters a particular heterologous pathogen than the first encounter. When one or more of these functions are destroyed, it will result in a physiological condition.

The virgin lymphocytes are continuously released from the primary lymphoid organs to the periphery, each carrying a surface receptor capable of binding to antigens. Antigen binding in B cells is mediated through surface-bound immunoglobulins, whereas in T cells it is mediated through T cell receptors. However, when virgin lymphocytes are activated, they proliferate to produce progeny cells, which can then undergo further activation and proliferation cycles. The rate and intensity of response to a given antigen is largely determined by clonal selection: the larger the clones of progeny cells or clones specific for a particular antigen are, the greater the number of cells that are able to recognize and participate in the immune response is. Each immune response is complex and complexly regulated by sequential events involving several cell types. The immune response is triggered when the immunogen enters the body and encounters specialized types of cells, called antigen presenting cells (APCs). A small amount of immunogen is captured by these APCs and displayed in a form that can be recognized by antigen-specific helper T lymphocytes. The helper T cells are then activated and in turn promote the activation of other types of lymphocytes, such as B cells or cytotoxic T cells. Activated lymphocytes then proliferate and perform their specific effector functions. At each stage of the process, lymphocytes and APCs communicate with each other through direct contact or through secretory regulatory cytokines.

Foreign antigens captured by APCs undergo a series of changes called antigen processing. Such processing (especially processing of protein immunogens) involves denaturation and partial proteolytic digestion whereby the immunogen is cleaved into short peptides. The resulting limited number of peptides are then non-covalently bound to the MHC class II proteins and transported to the APC surface, a process known as antigen presentation. CD4+ helper T lymphocytes that are in direct contact with APCs can be activated, but are only activated when expressing a T cell receptor protein that recognizes and binds to a specific peptide-MHC complex presented by APC.

Helper T (TH) cells are the main orchestrators of the immune response because they are required to activate two other effector lymphocytes: cytotoxic T (Tc) cells and antibody secretory plasma cells. TH activation occurs early in the immune response and requires at least two signals. One signal is provided by the binding of the T cell antigen receptor to the antigenic peptide-MHC complex delivered by the CD3 protein complex on the APC surface, while the second co-stimulatory signal by APC is believed to be derived from the binding of a separate signaling protein on the surface of T cells to a specific ligand on APC. One such known interaction is between the family of the APC surface protein known as B7 and the T cell protein CD28. Other surface protein pairings can also mediate co-stimulation. The process of co-stimulation is described in more detail below. The anti-PD-L1 antibodies described herein are believed to enhance co-stimulation by antagonizing negative co-stimulatory signals provided by signaling through PD-L1.

In summary, these two signals induce helper T cells to begin secreting the cytokine interleukin-2 (IL-2) and also begin to express specific high affinity IL-2 receptors on their surface. IL-2 is a highly potent mitogenic factor for T lymphocytes and is required for proliferative responses of activated T cells. The effect of IL-2 on cells secreting it is a phenomenon known as autocrine effect. It has also been shown that even though T cells have received both signals, they will not proliferate if their IL-2 receptors are blocked. IL-2 can also act on adjacent cells by a so-called paracrine effect. This effect is particularly important for the activation of Tc cells, which typically do not produce IL-2 sufficient to stimulate their own proliferation. In addition to IL-2, activated TH cells secrete other cytokines and promote the growth, differentiation and function of B cells, macrophages and other types of cells.

The contact between APCs and antigen-specific TH cells also has effects on APCs, and one of the most important effects is the release of IL-1. This cytokine is found to act in an autocrine manner to increase the surface expression of class II MHC proteins and various adhesion molecules thereby enhancing TH cell binding and antigen presentation. At the same time, IL-1 exerts a function on TH cells in a paracrine manner to promote IL-2 secretion and IL-2 receptor expression.

During the activation of TH cells in the manners described above, some B cells can also bind to the immunogen through their antigen receptors, which are antibodies in membrane-bound forms that will be secreted later. Unlike T cells, B cells recognize immunogens in their free, unprocessed form. Specific antigen binding provides a type of signal that can lead to B cell activation.

The second type is provided by activated TH cells that express a protein that assists in the activation of B cells by binding to a non-immunoglobulin receptor on their surface. These TH-derived signals, which act on B cells regardless of their antigen specificity, are known as cofactors. These cofactors include IL-2, IL-4 and IL-6. However, auxiliary effect is more efficiently obtained by cell-cell contact, which allows direct contact of proteins on the surface of T cells with those on B cells. The most effective form of contact-mediated auxiliary effect occurs when a protein known as CD40 ligand (CD40L, expressed on TH cells only after TH cells are activated) binds to proteins known as CD40 on B cells. In the process known as by-stander activation, contact with activated B cells can even be sufficient to activate resting B cells even if the surface immunoglobulin of the B cells has not bound to the antigen.

Tc lymphocytes function to eliminate cells that express heterologous antigens on their surface (such as virally infected host cells). Most Tc cells express CD8 rather than CD4, thus recognizing antigens associated with class I rather than class II MHC proteins. When somatic cells are infected with a virus, some of the immunogenic viral proteins can be processed intracellularly and the resulting peptides presented as surface complexes with class I MHC molecules. These peptide-MHC complexes can then be recognized by antigen-specific cloned T cell receptors, providing one of the two signals necessary for Tc-cell activation. The first signal alone induces a high affinity IL-2 receptor on Tc cells. The second signal is provided by IL-2 secreted from adjacent activated TH lymphocytes. Once the two signals are received, the activated Tc cells acquire cytotoxic activity, enabling them to kill the cells they bind to, as well as killing other cells carrying the same peptide-class I MHC complex. In some cases, killing occurs due to Tc releasing specific toxins to target cells; in other cases, Tc induces suicide of target cells through apoptosis. Activated Tc cells also proliferate, producing additional Tc cells with the same antigen specificity.

2. Pd-1 Pathway:

An important negative costimulatory signal that regulates T cell activation is provided by the programmed death-1 receptor (PD-1) (CD279) and its ligand binding partners PD-L1 (B7-H1, CD274) and PD-L2 (B7-DC, CD273). The negative regulation of PD-1 is revealed by a PD-1 knockout (Pdcd1−/−) that is susceptible to autoimmunity (Nishimura et al., Immunity 11: 141-51 (1999); Nishimura et al., Science 291: 319-22 (2001)). PD-1 is associated with CD28 and CTLA-4, but lacks a membrane-adjacent cysteine that allows homodimerization. The cytoplasmic domain of PD-1 contains an immunoreceptor tyrosine-based inhibitory motif (ITIM, V/IxYxxL/V). PD-1 only binds to PD-L1 and PD-L2 (Freeman et al., J. Exp. Med. 192: 1-9 (2000); Dong et al., Nature Med. 5: 1365-1369 (1999); Latchman et al., Nature Immunol. 2: 261-268 (2001); Tseng et al., J. Exp. Med. 193: 839-846 (2001)).

PD-1 can be expressed on T cells, B cells, natural killer T cells, activated monocytes, and dendritic cells (DCs). PD-1 is expressed by activated human CD4+ and CD8+ T cells, B cells and bone marrow cells, but not by these cells that are unstimulated. This is in contrast to the more restricted expression of CD28 and CTLA-4 (Nishimura et al., Int. Immunol. 8:773-80 (1996); Boettler et al., J. Virol. 80: 3532-40 (2006)). At least four variants of PD-1 have been cloned from activated human T cells, including transcripts lack of (i) exon 2, (ii) exon 3, (iii) exons 2 and 3; or (iv) exons 2 to 4 (Nielsen et al., Cell. Immunol. 235: 109-16 (2005)). Except for PD-1 Δex3, all variants were expressed at similar levels as full-length PD-1 in resting peripheral blood mononuclear cells (PBMCs). When human T cells were activated with anti-CD3 and anti-CD28, the expression of all variants was significantly induced. The PD-1 Δex3 variant lacks a transmembrane domain and is similar to soluble CTLA-4, which plays an important role in autoimmunity (Ueda et al., Nature 423:506-11 (2003)). This variant is enriched in synovial fluid and serum in patients with rheumatoid arthritis (Wan et al., J. Immunol. 177:8844-50 (2006)).

The difference between the two PD-1 ligands lies in their expression patterns. PD-L1 is constitutively expressed on mouse T and B cells, CDs, macrophages, mesenchymal stem cells, and bone marrow-derived mast cells (Yamazaki et al., J. Immunol. 169: 5538-45 (2002)). PD-L1 is expressed on a wide range of non-hematopoietic cells (e.g., cornea, lung, vascular epithelium, hepatic non-parenchymal cells, mesenchymal stem cells, islets, placental syncytial trophoblast cells, keratinocytes) [Keir et al., Annu. Rev. Immunol. 26: 677-704 (2008)] and up-regulated after activation of many cell types. Type I and Type II interferons (IFN's) up-regulate PD-L1 (Eppihimer et al., Microcirculation 9: 133-45 (2002); Schreiner et al., J. Neuroimmunol. 155: 172-82 (2004)). When MyD88, TRAF6 and MEK are inhibited, the expression of PD-L1 in the cells is reduced (Liu et al., Blood 110: 296-304 (2007)). JAK2 is also involved in PD-L1 induction (Lee et al., FEBS Lett. 580: 755-62 (2006); Liu et al., Blood 110: 296-304 (2007)). Loss or inhibition of phosphatase and tensin homolog (PTEN), a cellular phosphatase that modifies phosphatidylinositol 3-kinase (PI3K) and Akt signaling, increases post-transcriptional PD-L1 expression in cancers (Parsa et al., Nat. Med. 13: 84-88 (2007)).

PD-L2 expression is more restricted than PD-L1. PD-L2 induces expression on DCs, macrophages, and bone marrow-derived mast cells. PD-L2 is also expressed on approximately one-half to two-thirds of resting peritoneal B1 cells, but not on normal B2B cells (Zhong et al., Eur. J. Immunol. 37: 2405-10 (2007)). PD-L2+B1 cells bind to phosphatidylcholine and may be important for innate immune responses against bacterial antigens. The induction of PD-L2 by IFN-γ is partially dependent on NF-κB (Liang et al., Eur. J. Immunol. 33: 2706-16 (2003)). PD-L2 can also be induced on monocytes and macrophages by GM-CF, IL-4 and IFN-γ (Yamazaki et al., J. Immunol. 169: 5538-45 (2002); Loke et al., PNAS 100: 5336-41 (2003)).

PD-1 signaling typically has a greater effect on cytokine production than on cell proliferation and has a significant effect on IFN-γ, TNF-α and IL-2 production. PD-1-mediated inhibitory signaling also depends on the intensity of TCR signaling, which transmits greater inhibition at low levels of TCR stimulation. This reduction can be overcome by co-stimulation via CD28 [Freeman et al., J. Exp. Med. 192: 1027-34 (2000)] or the presence of IL-2 [Carter et al., Eur. J. Immunol. 32:634-43 (2002)].

Evidences showing that both PD-L1 and PD-L2 signaling may be bidirectional are increasing. That is, in addition to modification of TCR or BCR signaling, signaling may also be passed back to cells expressing PD-L1 and PD-L2. Although treatment of dendritic cells with natural human anti-PD-L2 antibody (isolated from patients with Waldenstrom's macroglobulinemia) did not reveal up-regulation of MHC II or B7 costimulatory molecules, such cells did produce a greater amount of pro-inflammatory cytokines, particularly TNF-α and IL-6, and stimulate T cell proliferation (Nguyen et al., J. Exp. Med. 196: 1393-98 (2002)). Treatment of mice with this antibody also (1) enhances resistance to transplanted b16 melanoma and rapidly induces tumor-specific CTL (Radhakrishnan et al., J. Immunol. 170: 1830-38 (2003); Radhakrishnan et al., Cancer Res. 64: 4965-72 (2004); Heckman et al., Eur. J. Immunol., 37: 1827-35 (2007)); (2) blocks the development of airway inflammatory diseases in a mouse model of allergic asthma (Radhakrishnan et al., J. Immunol. 173: 1360-65 (2004); Radhakrishnan et al., J. Allergy Clin. Immunol. 116: 668-74 (2005)).

Further evidence for reverse signaling to dendritic cells ("DC's") comes from studies of bone marrow-derived DCs cultured with soluble PD-1 (PD-1 EC domain fused to Ig constant region—"s-PD-1") (Kuipers et al., Eur. J. Immunol. 36: 2472-82 (2006)). This sPD-1 inhibits DC activation and increases IL-10 production in a manner that can be reversed by administration of anti-PD-1.

In addition, several studies have shown receptors for PD-L1 or PD-L2 that are independent of PD-1. B7.1 has been identified as a binding partner for PD-L1 (Butte et al., Immunity 27: 111-22 (2007)). Chemical cross-linking studies have shown that PD-L1 and B7.1 can interact through their IgV-like domains. The B7.1:PD-L1 interaction induces an inhibitory signal direct to T cells. Inhibitory signals are transmitted by B7.1 binding to PD-L1 on CD4$^+$ T cells or by PD-L1 binding to B7.1 on CD4$^+$ T cells. T cells lacking CD28 and CTLA-4 showed reduced proliferation and cytokine production when stimulated by anti-CD3 plus B7.1 coated beads. In T cells lacking all receptors for B7.1 (i.e., CD28, CTLA-4, and PD-L1), T cell proliferation and cytokine production were no longer inhibited by beads coated with anti-CD3 plus B7.1. This indicates that B7.1 on T cells acts specifically via PD-L1 in the absence of CD28 and CTLA-4. Similarly, when stimulated with anti-CD3 plus PD-L1 coated beads, T cells lacking PD-1 showed decreased proliferation and cytokine production, indicating the inhibitory effect of PD-L1 binding to T cells on B7.1. When T cells lack all known receptors for PD-L1 (i.e., no PD-1 and B7.1), T cell proliferation was no longer destroyed by anti-CD3 plus PD-L1 coated beads. Therefore, PD-L1 exerts an inhibitory effect on T cells through B7.1 or PD-1.

The direct interaction between B7.1 and PD-L1 suggests that the current understanding of co-stimulation is incomplete and underestimates the importance of the expression of these molecules for T cells. Studies of PD-L1−/− T cells have shown that PD-L1 on T cells can down-regulate T cell cytokine production (Latchman et al., Proc. Natl. Acad. Sci. USA 101: 10691-96 (2004)). Because both PD-L1 and B7.1 are expressed on T cells, B cells, DCs, and macrophages, there may be a directional interaction between B7.1 and PD-L1 on these cell types. In addition, PD-L1 on non-hematopoietic cells interacts with B7.1 and PD-1 on T cells, suggesting whether PD-L1 is involved in their regulation. One possible explanation for the inhibitory effect of B7.1: PD-L1 interaction is that T cell PD-L1 can capture or insulate APC B7.1 from interaction with CD28.

Thus, antagonizing PD-L1 signaling, including blocking PD-L1 from interaction with PD-1, B7.1, or both, thereby preventing PD-L1 from sending negative costimulatory signals to T cells and other antigen presenting cells may enhance immunity against infection (e.g., acute and chronic) and tumor immunity. Furthermore, the anti-PD-L1 antibodies described herein can be combined with antagonists of other components of PD-1:PD-L1 signaling, such as antagonistic anti-PD-1 and anti-PD-L2 antibodies.

Definitions

All technical terms used herein have the same meaning as understood by one of ordinary skill in the art. For specific definitions and terminology in the art, the professional can refer to Current Protocols in Molecular Biology (Ausubel). Abbreviations for amino acid residues are standard 3-letter and/or 1-letter codes used in the art to refer to one of the 20 commonly used L-amino acids.

The term "antibody" includes monoclonal antibodies (including full length antibodies having immunoglobulin Fc regions), multi-epitope specific antibody compositions, multispecific antibodies (e.g., bispecific antibodies), diabody and single-stranded molecules, as well as antibody fragments (e.g., Fab, F(ab')2, and Fv). The terms "immunoglobulin" (Ig) and "antibody" are used interchangeably herein.

The basic 4-chain antibody unit is a heterotetrameric glycoprotein composed of two identical light chains (L) and two identical heavy chains (H). The IgM antibody consists of 5 basic heterotetramer units and another polypeptide called J chain, which contains 10 antigen binding sites; and the IgA antibody contains 2-5 basic 4 chain units, which can be polymerized with the J chain to form a multivalent assembly. In the case of IgG, the 4-chain unit is typically about 150,000 daltons. Each light chain is linked to the heavy chain by a covalent disulfide bond, and the two heavy chains are linked to each other by one or more disulfide bonds, the number of disulfide bonds depending on the isotype of the heavy chain. Each heavy and light chain also has a regularly spaced intrachain disulfide bridge. Each heavy chain has a variable domain (VH) at the N-terminus, followed by three (for each α and γ chain) and four (for the μ and ε isoforms) constant domains (CHs). Each light chain has a variable domain (VL) at the N-terminus followed by a constant domain at the other end. VL is aligned with VH, and CL is aligned with the first constant domain (CH1) of the heavy chain. Particular amino acid residues are believed to form an interface between the light and heavy chain variable domains. The paired VH and VL together form an antigen binding site. For details on the structures and properties of different classes of antibodies, see, for example, Basic and Clinical Immunology, 8th Edition, Daniel P. Sties, Abba I. Ten and Tristram G. Parsolw (eds.), Appleton & Lange, Norwalk, Conn., 1994, pp. 71 and Chapter 6. Light chains from any vertebrate species, depending on their constant domain amino acid sequence, fall into one of two distinct forms called κ and λ. Immunoglobulins can be classified to different classes or isotypes depending on their heavy chain constant domain (CH) amino acid sequence. There are five classes of immunoglobulins: IgA, IgD, IgE, IgG, and IgM, with their heavy chains called α, δ, ε, γ and μ, respectively. Depending on the relatively small differences in CH sequence and function, γ and α classes can be further divided into subclasses; for example, humans express the following subclasses: IgG1, IgG2A, IgG2B, IgG3, IgG4, IgA1, and IgA2.

A "variable region" or "variable domain" of an antibody refers to the amino terminal domain of the heavy or light chain of an antibody. The variable domains of the heavy and light chains can be referred to as "VH" and "VL", respectively. These domains are typically the most variable part of the antibody (relative to other antibodies of the same type) and contain the antigen binding site.

The term "variable" refers to the situation where certain segments of the variable domain differ widely in antibody sequences. The V domain mediates antigen binding and defines the specificity of a particular antibody for its particular antigen. However, the variability is not evenly distributed across all amino acids spanned by the variable domain. Instead, it is concentrated in three segments called hypervariable regions (HVRs) (both in the light and heavy chain variable domains). The more highly conserved portion of the variable domains is called the framework region (FR). The variable domains of the native heavy and light chains each comprise four FR regions, which mostly adopt a beta-sheet conformation, joined by the formation of loops and in some cases by three HVRs forming part of the beta-sheet structure. The HVRs in each chain are held together very closely by the FR region and contribute to the formation of the antigen binding site of the antibody together with the HVRs of the other chain (see Kabat et al., Sequences of Immunological Interest, 5th Edition. National Institute of Health, Bethesda, Md. (1991)). The constant domains are not directly involved in the binding of antibodies to antigens, but exhibit multiple effector functions, such as the involvement of antibodies in antibody-dependent cell-mediated cytotoxicity.

The term "monoclonal antibody" as used herein, refers to an antibody obtained from a population of substantially homogeneous antibodies, i.e., in addition to possible naturally occurring mutations and/or post-translational modifications that may be present in minor amounts (e.g., isomerization, amidation), the individual antibodies that make up the population are identical. Monoclonal antibodies are highly specific and target a single antigenic site. Each monoclonal antibody is directed against a single determinant on the antigen as compared to polyclonal antibody preparations, which typically include different antibodies against different determinants (epitopes). In addition to their specificity, monoclonal antibodies have the advantage that they are synthesized by hybridoma culture and are not contaminated by other immunoglobulins. The modifier "monoclonal" indicates the character of the antibody obtained from a substantially homogeneous population of antibodies and should not be construed as requiring production of the antibody by any particular method. For example, monoclonal antibodies to be used in accordance with the disclosure can be produced by a variety of techniques including, for example, hybridoma methods (e.g., Kohler and Milstein, Nature, 256:495-97 (1975); Hongo et al., Hybridoma, 14(3): 253-260 (1995), Harlow et al., Antibodies: A Laboratory Manual, (Cold Spring Harbor Laboratory Press, 2nd Edition. 1988); Hammerling et al., in: Monoclonal Antibodies and T-Cell Hybridomas 563-681, (Elsevier, N Y, 1981)), recombinant DNA method (see, e.g., U.S. Pat. No. 4,816,567), phage display technology (See, for example, Clackson et al., Nature, 352: 624-628 (1991); Marks et al., J. Mol. Biol., 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Sci. USA, 101 (34): 12467-12472 (2004); and Lee et al., J. Immunol. Methods 284(1-2): 119-132 (2004)), and techniques for generating human or human-like antibodies from animals having partial or entire human immunoglobulin loci or genes encoding human immunoglobulin sequences (see, for example, WO 1998/24893; WO 1996/34096; WO 1996/33735; WO 1991/10741; Jakobovits et al., Proc. Natl. Acad. Sci. USA, 90:2551 (1993); Jakobovits et al., Nature, 362: 255-258 (1993); Bruggemann et al., Year in Immunol., 7:33 (1993); U.S. Pat. Nos. 5,545,807; 5,545,806; 5,569,825; 5,625,126; 5,633,425; and 5,661,016, Marks et al., Bio/Technology, 10: 779-783 (1992); Lonberg et al., Nature, 368: 856-859 (1994); Morrison, Nature, 368: 812-813 (1994); Fishwild et al., Nature Biotechnol., 14: 845-851 (1996); Neuberger, Nature Biotechnol., 14: 826 (1996); and Lonberg and Huszar, Intern. Rev. Immunol., 13: 65-93 (1995).

The terms "full length antibody", "intact antibody" or "complete antibody" are used interchangeably and refer to an antibody that is substantially in its intact form (as opposed to an antibody fragment). In particular, fully antibodies include those having heavy and light chains and Fc region. The constant domain can be a native sequence constant domain (e.g., a human native sequence constant domain) or an amino acid sequence variant thereof. In some cases, an intact antibody can have one or more effector functions.

An "antibody fragment" comprises a portion of an intact antibody, preferably an antigen binding region and/or a variable region of an intact antibody. Examples of antibody fragments include Fab, Fab', F(ab')2 and Fv fragments; diabodies; linear antibodies (see U.S. Pat. No. 5,641,870, Example 2; Zapata et al., Protein Eng. 8(10): 1057-1062 [1995]); single-chain antibody molecules; and multispecific antibodies formed from antibody fragments. Digestion of antibodies with papain produces two identical antigen-binding fragments called "Fab" fragments, and a residual "Fc" fragment whose name reflects its ability to crystallize readily. The Fab fragment consists of the entire light and heavy chain variable domain (VH) and the first constant domain (CH1) of one heavy chain. Each Fab fragment is monovalent in antigen binding, i.e., it has a single antigen binding site. Pepsin treatment of the antibody produces a larger F(ab')2 fragment that roughly corresponds to two Fab fragments joined by disulfide bonds, having different antigen binding activities and still capable of cross-linking antigen. The Fab' fragment differs from the Fab fragment by the addition of some additional residues at the carboxy terminus of the CH1 domain, including one or more cysteines from the antibody hinge region. The F(ab')2 antibody fragment was originally produced as a pair of Fab' fragments with a hinge cysteine between the Fab' fragments. Other chemical couplings of antibody fragments are also known. The Fc fragment comprises the carboxy terminal portions of the two heavy chains held together by a disulfide bond. The effector function of an antibody is determined by the sequence in the Fc region, which is also the region recognized by the Fc receptor (FcR) found on certain types of cells.

"Fv" is the smallest antibody fragment that contains the entire antigen recognition and binding site. This fragment consists of a dimer of a heavy chain variable domain that is tightly, non-covalently bound to a light chain variable domain. Six hypervariable loops (3 loops for each of the heavy and light chains) are protruded from the folding of these two domains, contributing to the antigen-binding amino acid residues and endowing the antibody with antigen binding specificity. However, even a single variable domain (or half of an Fv comprising only three HVRs specific for an antigen) has the ability to recognize and bind to an antigen, although the affinity is lower than the intact binding site.

"Single-chain Fv" may also be abbreviated as "sFv" or "scFv", which is an antibody fragment comprising an antibody VH and VL domain joined into a single polypeptide chain. Preferably, the sFv polypeptide further comprises a polypeptide linker between the VH and VL domains such that the sFv forms the desired antigen binding structure. For a review of sFv, see Pluckthun in The Pharmacology of Monoclonal Antibodies, vol. 113, Rosenburg and Moore, ed., Springer-Verlag, New York, pp. 269-315 (1994).

A "functional fragment" of an antibody described herein includes a portion of an intact antibody, typically comprising the antigen binding or variable region of the intact antibody, or the Fc region of the antibody, which retains or has a modified FcR binding ability. Examples of antibody fragments include linear antibodies, single-chain antibody molecules, and multispecific antibodies formed from antibody fragments. In particular, it refers to antibody fragments such as Fv, scFv (sc refers to single chain), Fab, F(ab')2, Fab', scFv-Fc fragment or diabody, or any fragment having increased half-life by incorporated into liposomes or modified chemically, such as the addition of poly(alkylene) glycols such as polyethylene glycol ("PEGylated") (pegylated fragment referred to as Fv-PEG, scFv-PEG, Fab-PEG, F(ab')2-PEG or Fab'-PEG) ("PEG" is polyethylene glycol), the fragment may have EGFR binding activity. Preferably, the functional fragment consists of or comprises a partial sequence of a heavy chain variable region or a light chain variable region of the antibody from which it is derived, the partial sequence being sufficient to retain the same binding specificity and sufficient affinity as the antibody from which it is derived (for PD-L1, it is preferably at least 1/100 of the affinity of the antibody from which it is derived, and in a more preferred embodiment at least 1/10). Such a functional fragment will comprise a minimum of 5 amino acids, preferably 10, 15, 25, 50 and 100 contiguous amino acids of the antibody sequence from which it is derived.

Monoclonal antibodies herein specifically include "chimeric" antibodies (immunoglobulins) in which a portion of the heavy and/or light chain is identical or homologous to the corresponding sequence in an antibody derived from a particular species or belonging to a particular antibody class or subclass, and the remainder of the chain is identical or homologous to the corresponding sequence in an antibody derived from another species or belonging to another antibody class or subclass, and fragments of such antibodies, as long as they exhibit the desired biology activity (U.S. Pat. No. 4,816,567; Morrison et al., Proc. Nat. Acad. Sci. USA 81:6851-6855 (1984)). A chimeric antibody of interest herein includes a PRIMATIZED antibody, wherein the antigen binding region of the antibody is derived from an antibody produced by, for example, immunizing macaques with an antigen of interest. As used herein, "humanized antibody" is used as a subset of "chimeric antibodies."

A "humanized" form of a non-human (e.g., murine) antibody refers to a chimeric antibody that minimally comprises sequences derived from a non-human immunoglobulin.

"Human antibody" refers to an antibody that has an amino acid sequence corresponding to the amino acid sequence of a human-derived antibody and/or is produced using any of the techniques disclosed herein for the production of human antibodies. This definition of a human antibody specifically excludes a humanized antibody comprising non-human antigen-binding residue(s). Human antibodies can be generated using a variety of techniques known in the art, including phage display libraries (Hoogenboom and Winter, J. Mol. Biol. 227: 381 (1991); Marks et al., J. Mol. Biol. 222: 581 (1991)). Available methods for preparing human monoclonal antibodies are described in Cole et al., Monoclonal Antibodies and Cancer Therapy, Alan R. Liss, p. 77 (1985); Boerner et al., J. Immunol. 147(1): 86-95 (1991). See also van Dijk and van de Winkel, Curr. Opin. Pharmacol., 5: 368-74 (2001). Human antibodies can be prepared by administering an antigen to a transgenic animal modified to produce such antibodies in response to an antigen, but whose endogenous locus has been disabled, such as an immunized xennomice (see, e.g., U.S. Pat. Nos. 6,075,181 and 6,150,584, on XENOMOUSE™ technology). See also, for example, Li et al., Proc. Natl. Acad. Sci. USA, 103: 3557-3562 (2006) for human antibodies produced by human B cell hybridoma technology.

"Framework" or "FR" residues refer to those variable domain residues other than the HVR residues defined herein.

The disclosure provides an anti-PD-L1 antibody capable of binding to PD-L1 and a functional fragment thereof. The antibody described herein or a functional fragment thereof has at least one of the following properties: capable of blocking the interaction of PD-L1 and PD-1 with high affinity; capable of binding with PD-L1 with high specificity.

Also provided are humanized anti-PD-L1 antibodies and functional fragments thereof. The humanized antibody is obtained from a mouse-derived antibody produced by immunizing mice via computer simulation design in conjunction with phage display technology.

One of skill in the art can replace, add, and/or delete one or more (e.g., 1, 2, 3, 4, 5, 6, 7, 8, 9 or 10 or more) amino acids of the sequences described herein without substantial impact on antibody activity to obtain variants of the sequence of the antibody or a functional fragment thereof. They are all considered to be included within the scope of the invention. For example, amino acid(s) in the variable region are replaced with amino acid(s) having similar properties. The sequences of the variants described herein may be at least 95%, 96%, 97%, 98% or 99% identical to the sequence from which they are derived. The sequence identity described herein can be measured using sequence analysis software. For example, the computer program BLAST using default parameters, especially BLASTP or TBLASTN.

The antibodies described herein may be in full length (e.g., IgG1 or IgG4 antibodies) or may comprise only antigen binding portions (e.g., Fab, F(ab')$_2$ or scFv fragments), or may be modified to affect function. The disclosure encompasses an anti-PD-L1 antibody having a modified glycosylation pattern. In some applications, it can be useful to make modifications to remove undesired glycosylation sites, or to make the oligosaccharide chain to have no fucose moiety thereon to, for example, enhance antibody-dependent cellular cytotoxicity (ADCC) function. In other applications, galactosylation modifications can be made to alter complement dependent cytotoxicity (CDC).

A person skilled in the art can clone a DNA molecule encoding the anti-PD-L1 antibody described herein into a vector, which is to be transformed into a host cell. Accordingly, the disclosure also provides a recombinant DNA vector comprising a DNA molecule encoding the anti-PD-L1 antibody described herein.

Preferably, the recombinant DNA vector is an expression vector. A person skilled in the art clones the DNA molecule of the antibody into an expression vector, transforms the host cell with the expression vector, and obtains an antibody by inducing expression. The expression vector described herein contains a DNA sequence encoding a heavy chain variable region, a light chain variable region and/or a constant region of an anti-PD-L1 antibody. However, it is also possible to construct two expression vectors, one encoding a heavy chain variable region and a constant region, and the other encoding a light chain variable region and a constant region, for co-transfection of mammalian cells. In a preferred embodiment, the expression vector further comprises a promoter and a DNA sequence encoding a secretion signal peptide, and at least one drug resistance gene for screening.

The host cell described herein may be a prokaryotic host cell, a eukaryotic host cell or a bacteriophage. The prokaryotic host cell may be *Escherichia coli, Bacillus subtilis, Streptomyces, Proteus mirabilis*, and the like. The eukaryotic host cell may be a fungus such as *Pichia pastoris, Saccharomyces cerevisiae, Schizogenesis pombe, Trichoderma*; insect cells, such as grass armyworm cells; plant cells, such as tobacco cells; mammalian cells, such as BHK cells, CHO cells, COS cells and myeloma cells. In some embodiments, the host cell described herein is preferably a mammalian cell, more preferably a BHK cell, a CHO cell, an NSO cell, or a COS cell.

The term "pharmaceutical composition" as used herein, denotes a combination of at least one drug and optionally a pharmaceutically acceptable carrier or excipient that are combined together to achieve a particular purpose. In certain embodiments, the pharmaceutical compositions include combinations that are separated in time and/or space, as long as they are capable of acting together to achieve the objectives of the disclosure. For example, the components contained in the pharmaceutical composition (e.g., antibodies, nucleic acid molecules, nucleic acid molecule combinations, and/or conjugates described herein) can be administered as a whole or separately to a subject. When the components contained in the pharmaceutical composition are separately administered to a subject, the components may be administered to the subject simultaneously or sequentially. Preferably, the pharmaceutically acceptable carrier is water, a buffered aqueous solution, an isotonic saline solution such as PBS (phosphate buffer), dextrose, mannitol, dextrose, lactose, starch, magnesium stearate, cellulose, magnesium carbonate, 0.3% glycerol, hyaluronic acid, ethanol or polyalkylene glycols (such as polypropylene glycol), triglycerides and the like. The type of pharmaceutically acceptable carrier used herein depends inter alia on whether the composition described herein is formulated for oral, nasal, intradermal, subcutaneous, intramuscular or intravenous administration. The composition described herein may comprise a wetting agent, an emulsifier or a buffering substance as an additive.

The pharmaceutical composition described herein may be administered by any suitable route, for example, orally, nasally, intradermally, subcutaneously, intramuscularly or intravenously.

In a related aspect, the disclosure provides a pharmaceutical composition that is a combination of an anti-PD-L1 antibody and a second therapeutic agent. In one embodiment, the second therapeutic agent is any agent that is advantageously combined with an anti-PD-L1 antibody. Exemplary agents that may be advantageously combined with an anti-PD-L1 antibody include, but are not limited to, other agents that inhibit PD-L1 activity (including other antibodies or antigen-binding fragments thereof, peptide inhibitors, small molecule antagonists, etc.) and/or agents that interfere with PD-L1 upstream or downstream signaling.

The term "preventing or treating a disease or condition by eliminating, inhibiting or reducing PD-L1 activity" as used herein is intended to mean a disease or condition caused by PD-L1 expression or characterized by PD-L1 expression, including T cell dysfunctional diseases such as cancer and inflammatory diseases. In some embodiments, the cancer of the disclosure includes, but is not limited to, gastric cancer, lung cancer, liver cancer, intrahepatic cholangiocarcinoma, colon cancer, pancreatic cancer, ovarian cancer, breast cancer, cervical cancer, head and neck squamous cell carcinoma, nasopharyngeal cancer, esophageal cancer, bladder cancer, renal cell carcinoma, skin cancer and oral squamous cell carcinoma.

As used herein, "therapeutically effective amount" refers to a dose sufficient to demonstrate its benefit to the subject to which it is administered. The actual amount administered, as well as the rate and time course of administration, will depend on the condition and severity of the subject being treated. The prescription for treatment (e.g., the determination of the dose, etc.) is ultimately the responsibility of the general practitioner and other physicians and depends on their decision, usually considering the disease being treated, the condition of the individual patient, the site of delivery, the method of administration, and other factors known by the physician.

The term "subject" as used herein refers to a mammal, such as a human, but may also be other animals, such as wild animals (such as herons, storks, cranes, etc.), livestock (such as ducks, geese, etc.) or experimental animals (such as orangutans, monkeys, rats, mice, rabbits, guinea pigs, etc.).

In one aspect, the antibody or a functional fragment thereof described herein comprises heavy chain CDR(s) selected from amino acid sequences of SEQ ID NOs: 7, 8, 9, 13, 14, 15, 19, 20, 21, 22, 23, 24, 28, 29 and 30 or any variants thereof, and/or light chain CDR(s) selected from an amino acid sequence of SEQ ID NOs: 1, 2, 3, 4, 5, 6, 10, 11, 12, 16, 17, 18, 25, 26 and 27 or any variants thereof. In certain preferred embodiments, the amino acid sequences of the heavy chain CDRs of the antibody or a functional fragment thereof are selected from the group consisting of SEQ ID NOs: 7, 8, 9, 13, 14, 15, 19, 20, 21, 22, 23, 24, 28, 29 and 30, and/or the amino acid sequences of the light chain CDRs are selected from the group consisting of SEQ ID NOs: 1, 2, 3, 4, 5, 6, 10, 11, 12, 16, 17, 18, 25, 26 and 27.

In some preferred embodiments, the amino acid sequence of the heavy chain CDR1 of an antibody described herein or a functional fragment thereof is set forth in SEQ ID NOs: 7, 13, 19, 22 or 28 or any variants thereof. In some preferred embodiments, the amino acid sequence of the heavy chain CDR2 of an antibody described herein or a functional fragment thereof is set forth in SEQ ID NOs: 8, 14, 20, 23 or 29 or any variants thereof. The amino acid sequence of the heavy chain CDR3 of an antibody described herein or a functional fragment thereof is set forth in SEQ ID NOs: 9, 15, 21, 24 or 30 or any variants thereof.

In some preferred embodiments, the amino acid sequence of the heavy chain CDR1 of an antibody described herein or a functional fragment thereof is set forth in SEQ ID NOs: 7, 13, 19, 22 or 28 or any variants thereof; the amino acid sequence of the heavy chain CDR2 is set forth in SEQ ID NOs: 8, 14, 20, 23 or 29 or any variants thereof; and the amino acid sequence of the heavy chain CDR3 is set forth in SEQ ID NOs: 9, 15, 21, 24 or 30 or any variants thereof.

In some preferred embodiments, the amino acid sequences of the heavy chain CDR1, CDR2 and CDR3 of the antibody or a functional fragment thereof are selected from one of the following groups of amino acid sequences or variants thereof:

| Group | HCDR1 | HCDR2 | HCDR3 |
|---|---|---|---|
| A | SEQ ID NO: 7 | SEQ ID NO: 8 | SEQ ID NO: 9 |
| B | SEQ ID NO: 13 | SEQ ID NO: 14 | SEQ ID NO: 15 |
| C | SEQ ID NO: 19 | SEQ ID NO: 20 | SEQ ID NO: 21 |
| D | SEQ ID NO: 22 | SEQ ID NO: 23 | SEQ ID NO: 24 |
| E | SEQ ID NO: 28 | SEQ ID NO: 29 | SEQ ID NO: 30 |

In some preferred embodiments, the amino acid sequence of the light chain CDR1 of an antibody described herein or a functional fragment thereof is set forth in SEQ ID NOs: 1, 4, 10, 16 or 25 or any variants thereof. In some preferred embodiments, the amino acid sequence of the light chain CDR2 of an antibody described herein or a functional fragment thereof is set forth in SEQ ID NOs: 2, 5, 11, 17, or 26 or any variants thereof. The amino acid sequence of the light chain CDR3 of an antibody described herein or a functional fragment thereof is as set forin in SEQ ID NOs: 3, 6, 12, 18 or 27 or any variants thereof.

In some preferred embodiments, the amino acid sequence of the light chain CDR1 of an antibody described herein or a functional fragment thereof is set forth in SEQ ID NOs: 1, 4, 10, 16 or 25 or any variants thereof; the amino acid sequence of the light chain CDR2 is set forth in SEQ ID NOs: 2, 5, 11, 17, or 26 or any variants thereof; and the amino acid sequence of the light chain CDR3 is set forth in SEQ ID NOs: 3, 6, 12, 18 or 27 or any variants thereof.

In some preferred embodiments, the amino acid sequences of the light chain CDR1, CDR2, and CDR3 of the antibody or a functional fragment thereof are selected from one of the following groups of amino acid sequences or variants thereof:

| Group | LCDR1 | LCDR2 | LCDR3 |
|---|---|---|---|
| F | SEQ ID NO: 1 | SEQ ID NO: 2 | SEQ ID NO: 3 |
| G | SEQ ID NO: 4 | SEQ ID NO: 5 | SEQ ID NO: 6 |
| H | SEQ ID NO: 10 | SEQ ID NO: 11 | SEQ ID NO: 12 |
| I | SEQ ID NO: 16 | SEQ ID NO: 17 | SEQ ID NO: 18 |
| J | SEQ ID NO: 25 | SEQ ID NO: 26 | SEQ ID NO: 27 |

In some preferred embodiments, the amino acid sequence of the heavy chain CDR1 of an antibody described herein or a functional fragment thereof is set forth in SEQ ID NOs: 7, 13, 19, 22 or 28 or any variants thereof; the amino acid sequence of the heavy chain CDR2 is set forth in SEQ ID NOs: 8, 14, 20, 23 or 29 or any variants thereof; and the amino acid sequence of the heavy chain CDR3 is set forth in SEQ ID NOs: 9, 15, 21, 24 or 30 or any variants thereof; and the amino acid sequence of the light chain CDR1 is set forth in SEQ ID NOs: 1, 4, 10, 16 or 25 or any variants thereof; the amino acid sequence of the light chain CDR2 is set forth in SEQ ID NOs: 2, 5, 11, 17, or 26 or any variants thereof; and the amino acid sequence of the light chain CDR3 is set forth in SEQ ID NOs: 3, 6, 12, 18 or 27 or any variants thereof.

In some preferred embodiments, the amino acid sequences of the heavy chain CDR1, CDR2 and CDR3 of the antibody or a functional fragment thereof are selected from one of the following groups of amino acid sequences or variants thereof:

| Group | HCDR1 | HCDR2 | HCDR3 |
|---|---|---|---|
| A | SEQ ID NO: 7 | SEQ ID NO: 8 | SEQ ID NO: 9 |
| B | SEQ ID NO: 13 | SEQ ID NO: 14 | SEQ ID NO: 15 |
| C | SEQ ID NO: 19 | SEQ ID NO: 20 | SEQ ID NO: 21 |
| D | SEQ ID NO: 22 | SEQ ID NO: 23 | SEQ ID NO: 24 |
| E | SEQ ID NO: 28 | SEQ ID NO: 29 | SEQ ID NO: 30 | and/or the amino acid sequences of the light chain CDR1, CDR2 and CDR3 are selected from one of the following groups of amino acid sequences or variants thereof:

| Group | LCDR1 | LCDR2 | LCDR3 |
|---|---|---|---|
| F | SEQ ID NO: 1 | SEQ ID NO: 2 | SEQ ID NO: 3 |
| G | SEQ ID NO: 4 | SEQ ID NO: 5 | SEQ ID NO: 6 |
| H | SEQ ID NO: 10 | SEQ ID NO: 11 | SEQ ID NO: 12 |
| I | SEQ ID NO: 16 | SEQ ID NO: 17 | SEQ ID NO: 18 |
| J | SEQ ID NO: 25 | SEQ ID NO: 26 | SEQ ID NO: 27 |

In some preferred embodiments, the amino acid sequences of the heavy chain CDR1, CDR2 and CDR3 and the light chain CDR1, CDR2 and CDR3 of the antibody or a functional fragment thereof described herein are selected from one of the following groups of amino acid sequences or variants thereof:

| Group | LCDR1 | LCDR2 | LCDR3 | HCDR1 | HCDR2 | HCDR3 |
|---|---|---|---|---|---|---|
| 1 | SEQ ID NO: 1 | SEQ ID NO: 2 | SEQ ID NO: 3 | SEQ ID NO: 7 | SEQ ID NO: 8 | SEQ ID NO: 9 |
| 2 | SEQ ID NO: 4 | SEQ ID NO: 5 | SEQ ID NO: 6 | SEQ ID NO: 7 | SEQ ID NO: 8 | SEQ ID NO: 9 |
| 3 | SEQ ID NO: 10 | SEQ ID NO: 11 | SEQ ID NO: 12 | SEQ ID NO: 13 | SEQ ID NO: 14 | SEQ ID NO: 15 |
| 4 | SEQ ID NO: 16 | SEQ ID NO: 17 | SEQ ID NO: 18 | SEQ ID NO: 19 | SEQ ID NO: 20 | SEQ ID NO: 21 |
| 5 | SEQ ID NO: 16 | SEQ ID NO: 17 | SEQ ID NO: 18 | SEQ ID NO: 22 | SEQ ID NO: 23 | SEQ ID NO: 24 |
| 6 | SEQ ID NO: 25 | SEQ ID NO: 26 | SEQ ID NO: 27 | SEQ ID NO: 28 | SEQ ID NO: 29 | SEQ ID NO: 30 |

In some embodiments, an antibody described herein or a functional fragment thereof comprises the heavy chain variable region of an amino acid sequence selected from the group consisting of SEQ ID NOs: 33, 35, 37, 38, 40, or any variants thereof, and/or the light chain variable region of an amino acid sequence selected from the group consisting of SEQ ID NOs: 31, 32, 34, 36, 39, or any variants thereof. In certain embodiments, the amino acid sequence of the heavy chain variable region of an antibody described herein or a functional fragment thereof is set forth in SEQ ID NOs: 33, 35, 37, 38 or 40, and/or the amino acid sequence of the light chain variable region of the antibody or a functional fragment thereof is set forth in SEQ ID NOs: 31, 32, 34, 36 or 39.

In a preferred embodiment, the heavy chain variable region is SEQ ID NO: 33 or a variant thereof and the light chain variable region is SEQ ID NO: 31 or a variant thereof.

In another preferred embodiment, the heavy chain variable region is SEQ ID NO: 33 or a variant thereof and the light chain variable region is SEQ ID NO: 32 or a variant thereof.

In yet another preferred embodiment, the heavy chain variable region is SEQ ID NO: 35 or a variant thereof and the light chain variable region is SEQ ID NO: 34 or a variant thereof.

In yet another preferred embodiment, the heavy chain variable region is SEQ ID NO: 37 or a variant thereof and the light chain variable region is SEQ ID NO: 36 or a variant thereof.

In yet another preferred embodiment, the heavy chain variable region is SEQ ID NO: 38 or a variant thereof and the light chain variable region is SEQ ID NO: 36 or a variant thereof.

In yet another preferred embodiment, the heavy chain variable region is SEQ ID NO: 40 or a variant thereof and the light chain variable region is SEQ ID NO: 39 or a variant thereof.

The antibody described herein or a functional fragment thereof can be a chimeric antibody, a humanized antibody or a fully human antibody.

The antibodies described herein or functional fragments thereof can be humanized. Methods of making humanized antibodies are well known to a person skilled in the art. For example, a humanized anti-PD-L1 antibody described herein can be prepared by transferring the CDR sequences described herein into the variable regions of a human antibody. The humanized antibody does not produce an anti-antibody reaction (AAR) and a human anti-mouse antibody response (HAMA), and will not be rapidly cleared by neutralization of an anti-antibody, and has an immunological effector function.

In some preferred embodiments, the humanized anti-PD-L1 antibody or functional fragment thereof described herein comprises the heavy chain variable region of an amino acid sequence selected from the group consisting of SEQ ID NOs: 33, 35, 37, 38 and 40, or any variants thereof, and/or the light chain variable region of an amino acid sequence selected from the group consisting of SEQ ID NOs: 31, 32, 34, 36, 39, or an variant of any of the sequences. In certain embodiments, the amino acid sequence of the heavy chain variable region of a humanized anti-PD-L1 antibody or a functional fragment thereof described herein is set forth in SEQ ID NOs: 33, 35, 37, 38 or 40, and/or the amino acid sequence of the light chain variable region thereof is set forth in SEQ ID NOs: 31, 32, 34, 36 or 39.

In a preferred embodiment of the humanized antibody described herein or a functional fragment thereof, the heavy chain variable region is SEQ ID NO: 33 or a variant thereof and the light chain variable region is SEQ ID NO: 31 or a variant thereof.

In a preferred embodiment of the humanized antibody described herein or a functional fragment thereof, the heavy chain variable region is SEQ ID NO: 33 or a variant thereof and the light chain variable region is SEQ ID NO: 32 or a variant thereof.

In another preferred embodiment of the humanized antibody described herein or a functional fragment thereof, the heavy chain variable region is SEQ ID NO: 35 or a variant thereof and the light chain variable region is SEQ ID NO: 34 or a variant thereof.

In another preferred embodiment of the humanized antibody described herein or a functional fragment thereof, the heavy chain variable region is SEQ ID NO: 38 or a variant thereof and the light chain variable region is SEQ ID NO: 36 or a variant thereof.

In yet another preferred embodiment of the humanized antibody described herein or a functional fragment thereof, the heavy chain variable region is SEQ ID NO: 37 or a variant thereof and the light chain variable region is SEQ ID NO: 36 or a variant thereof.

In yet another preferred embodiment of the humanized antibody described herein or a functional fragment thereof, the heavy chain variable region is SEQ ID NO: 40 or a variant thereof and the light chain variable region is SEQ ID NO: 39 or a variant thereof.

In yet another preferred embodiment of the humanized antibody described herein or a functional fragment thereof, the heavy chain variable region is SEQ ID NO: 44 or a variant thereof and the light chain variable region is SEQ ID NO: 42 or a variant thereof.

In yet another preferred embodiment of the humanized antibody described herein or a functional fragment thereof, the heavy chain variable region is SEQ ID NO: 48 or a variant thereof and the light chain variable region is SEQ ID NO: 46 or a variant thereof.

Also provided is an isolated nucleic acid molecule encoding an antibody described herein or a functional fragment thereof. Accordingly, provided herein is nucleic acid molecules encoding the CDRs, light chain variable regions or heavy chain variable regions described herein, including but not limited to the nucleic acid molecules encoding the amino acid sequences set forth in SEQ ID NOs: 1-40, 42, 44, 46 and 48. In a preferred embodiment, the nucleic acid molecule comprises the nucleotide sequence set forth in SEQ ID NOs: 43, 47 and/or 45, 49, or a combination thereof. In certain embodiments, the nucleic acid molecule described herein is set forth in SEQ ID NOs: 43, 47, 45 or 49.

Also provided is an expression vector comprising the nucleic acid molecule and a host cell comprising the expression vector.

Provided is a method of producing an anti-PD-L1 antibody or a functional fragment thereof, comprising: cultivating the above-described host cell under conditions permitting the production of the antibody or a functional fragment thereof, and recovering the resulting antibody or functional fragment thereof.

In another aspect, the disclosure relates to an immunoconjugate comprising an antibody described herein or a functional fragment thereof conjugated to a therapeutic agent. The therapeutic agent is preferably a toxin, a radioisotope, a drug or a cytotoxic agent.

The disclosure further relates to a pharmaceutical composition comprising an antibody described herein or a functional fragment thereof, and a pharmaceutically acceptable carrier.

In another aspect, provided herein is a method for preventing or treating a disease or condition by eliminating, inhibiting or reducing PD-L1 activity, comprising administering to a subject in need thereof a therapeutically effective amount of an antibody or a functional fragment thereof, a nucleic acid, an expression vector, a host cell, an immunoconjugate or a pharmaceutical composition described herein.

Also provided is the use of an antibody or a functional fragment thereof, a nucleic acid, an expression vector, a host cell, an immunoconjugate or a pharmaceutical composition described herein, for the manufacture of a medicament for the treatment of a disease or condition.

The following examples are provided to demonstrate and further illustrate some of the preferred embodiments and aspects of the disclosure and are not to be interpreted as limiting.

Figure 1B:
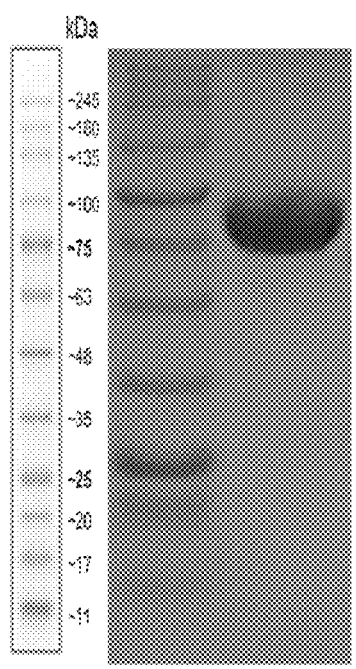
FIG. 1B: SDS-PAGE electropherogram of human PD-L1 extracellular domain protein.

Example 1. Cloning the Extracellular Domain of Human PD-L1 into Eukaryotic Expression Plasmid Plasmid HG10084-M containing the cDNA sequence of human PD-L1 gene was purchased from Yiqiao Shenzhou; a human PD-L1 extracellular fragment (nucleotide sequence is shown in SEQ ID NO: 41) was amplified by PCR using the forward primer 5'-GTACGCTAGCCACCATGAGGAT-ATTTGCTGTC-3' (SEQ ID NO: 50) and reverse primer 5'-GATCCTCGAGCGTGAGTCCTTTCATTTGG-3' (SEQ ID NO: 51). The amplified fragment was digested with NheI and XhoI, and cloned into the self-constructed eukaryotic expression plasmid system (pSec CAGA2 ECD, which was engineered based on the pCDNA3.1 plasmid, as shown in FIG. 1A), and the plasmid was transfected into 293 E cells through PEI. After 6 days, the culture supernatant was collected and purified by affinity chromatography to obtain a human PD-L1 extracellular domain protein. As shown in FIG. 1B, the size of the human PD-L1 extracellular region protein is about 75 K Daltons by SDS-PAGE staining with Coomassie brilliant blue.

Example 2. ELISA for the Detection of Binding of Human PD-L1 Recombinant Protein to Human PD-1

2.1 Biotinylated Human PD-L1 Recombinant Protein

The human PD-L1 recombinant protein (i.e., the human PD-L1 extracellular domain protein obtained in Example 1) and the biotin-NHS dissolved in DMSO were mixed in a molar ratio of 1:10, and placed at 4° C. for 2 hours. The reaction mixture was passed through a 10 kD ultrafiltration column to separate biotinylated human PD-L1 and free biotin.

2.2 ELISA Detection of Binding of Biotin-Labeled Human PD-L1 to PD-1

To examine the binding ability of human PD-L1 to PD-1, 2 µg/ml of PD-1 was plated on a 96-well microtiter plate in a coating buffer at 4° C. overnight. The next day, the solution in the wells was discarded and the wells were washed 3 times with washing buffer. The wells were then blocked by adding PBS solution containing 2% milk for 60 minutes. After washing 3 times with washing buffer, the wells were added with 100 µl of biotin-labeled human PD-L1 of different concentrations, incubated for 1 hour at room temperature, washed 3 times with washing buffer, and added with HRP-streptavim diluted 1 to 10000 times with the washing buffer. The wells were incubated for 1 hour at room temperature, washed 3 times with washing buffer, and 50 µl of TMB substrate solution was added for color development. After reacting for 8 minutes at room temperature, the reaction was terminated with 100 µl of 2 M hydrochloric acid solution and the absorbance was read at 450 nm.

Figure 2:
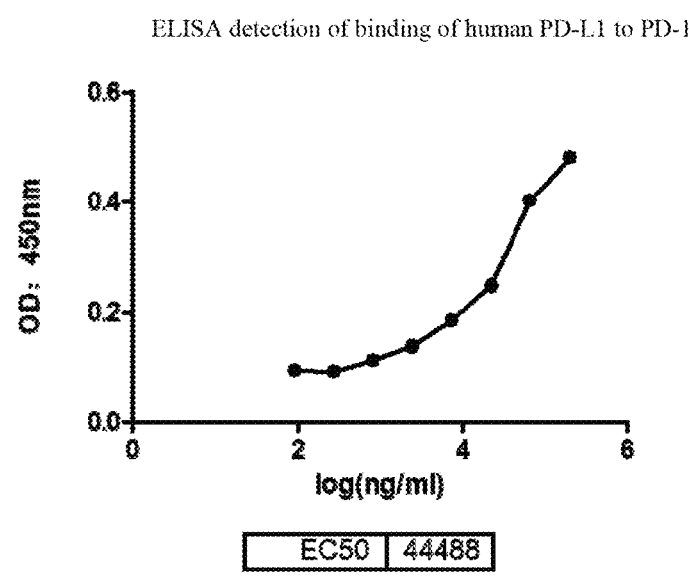
FIG. 2: Elisa detection of binding of human PD-L1 extracellular domain protein to PD-1.

The results are shown in FIG. 2, indicating that the biotinylated human PD-L1 recombinant protein specifically binds to PD-1.

Example 3. Cell Level Detection of Binding of PD-L1 to PD-1

3.1 Construction of 293F Human PD-1 Stable Cell Line

The eukaryotic expression plasmid constructed with the full-length PD-1 sequence with the puromycin-selective screening system was transfected into 293F adherent cells by PEI. After 24 h of transfection, screening was performed by puromycin (2 µg/ml) until a 293F PD-1 stable cell bank was formed. At the same time, a 96-well plate was prepared by limiting dilution method at 0.8 cells per well. After 15 days, 293F PD-1 monoclonal was selected and passaged to form a 293F PD-1 stable cell line.

3.2 Binding of Biotinylated Human PD-L1 to 293F PD-1 Stable Strain

Biotin-labeled human PD-L1 recombinant protein (i.e., human PD-L1 extracellular domain protein obtained in Example 1) of different concentrations and 293F PD-1 stable cell suspension were mixed and incubated at 37° C. for 30 minutes. After eluting 3 times by FACS buffer (20 mM Tris, 100 mM NaCl, 2 mM $Ca^{2+}$, 1% FBS, pH 7.4), streptavidin-allophycocyanin (SA-APC, 2 µg/ml) was added and incubated at room temperature for 30 minutes. After eluting 3 times with FACS buffer, the cells were analyzed on a flow cytometer.

Figure 3:
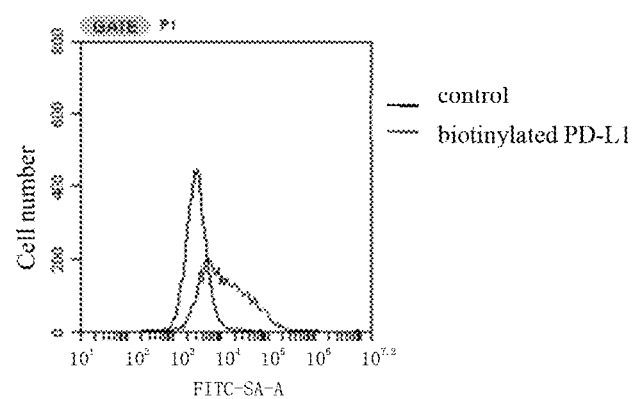
FIG. 3: FACS detection of binding of human PD-L1 extracellular domain protein to PD-1 on 293F cells.

The results are shown in FIG. 3, indicating that biotinylated PD-L1 can specifically bind to PD-1 on 293F cells.

Example 4. Preparation of Anti-PD-L1 Murine Antibody 4.1 Immunization of Animals The human PD-L1 recombinant protein obtained in Example 1 was mixed as an antigen with an equal amount of immunological adjuvant (Freund's adjuvant), and used to immunize five 6-week-old female FVB mice. After the initial immunization, booster immunizations were performed once a week for a total of four immunizations.

4.2 Cell Fusion

After the last booster immunization, the lymph nodes at the roots of the thighs of the mice were taken. The lymphocyte-rich suspension was obtained after ground the lymph nodes in physiological saline, and was subjected to conventional electroporation (see BTX company's electro-transfer manual) for SP2/0 cell fusion. The fused cells were cultured in RPMI-1640 complete medium (Sigma) containing HAT under 5% $CO_2$ at 37° C.

Example 5. Screening Experiment of Hybridoma Cells

In 12,000 different monoclonal hybridoma cells, 950 clones which secreted antibodies capable of binding to human PD-L1 protein were screened by ELISA reaction. Of these 950 clones, 139 were able to bind to PD-L1 expressed on 293F cells; of these 139 clones, 23 clones showed the ability to inhibit the binding of biotinylated human PD-L1 to PD-1 on 293 cells. We focused on these 23 clones for subsequent experiments.

The antibodies of the 23 clones obtained above were directly mixed with biotin-labeled human PD-L1 (10 µg/ml), and incubated at room temperature for 30 minutes. The mixture was then incubated with the PD-1 stably transfected 293F cell strain suspension for 30 minutes at 37° C. After washing the cells three times with FACS buffer, 5 µg/ml of SA-APC was added and incubated for 30 minutes. After washed three times with FACS buffer, the cells were detected by flow cytometry to verify whether the antibodies secreted by the hybridoma cells can inhibit the binding of human PD-L1 to PD-1 on the surface of 293F cells.

Figure 4:
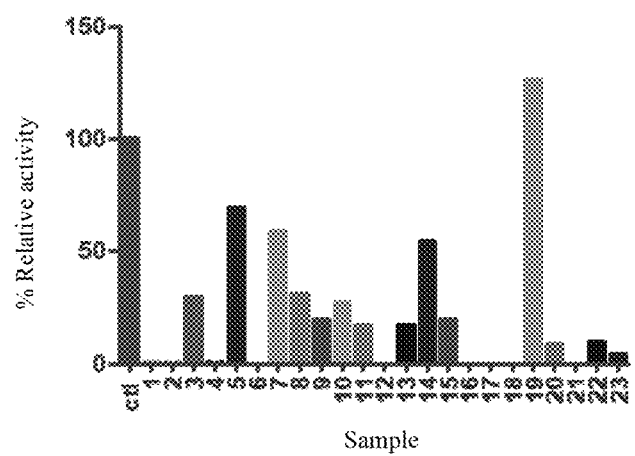
FIG. 4: FACS detection of the effect of candidate hybridoma cell supernatants in inhibiting the binding of PD-L1 to PD-1.

The results are shown in FIG. 4. The results showed that clones 1, 2, 4, 6, 16, 17, 18, 21 had a good inhibitory effect on the binding of PD-L1 to PD-1 on 293F cells.

Example 6. Jurkat Fluorescein Analysis of Candidate Antibodies

CHO cells expressing PD-L1 were plated into 96-well plates at a cell amount of $5\times10^4$, cultured at 37° C., 7% $CO_2$ overnight, and the cell supernatant was removed. Forty microlitre of antibody dilution was added to each well (starting concentration was 60 μg/ml, with a 3 fold concentration gradient dilution). Forty microlitre of Jurkat reporter cells (purchased from Promega) capable of continuously expressing PD-1 and NFAT-luciferase reporter genes were added with a total cell number of $1\times10^5$ cells and cultured at 37° C., 7% $CO_2$ for 6 hours before the addition of luciferase reagent and the detection of luminescence value by a microplate reader.

Figure 5:
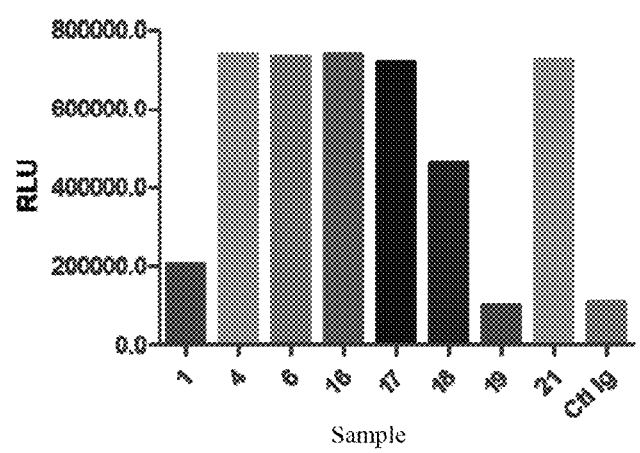
FIG. 5: Jurkat fluorescein analysis of candidate hybridoma cell supernatants.

The results are shown in FIG. 5. The results of fluorescein assay showed that clones 4, 6, 16, 17, 18 and 21 significantly restore the luciferase expression in Jurkat cells inhibited by PD-L1.

Example 7. Determination of Binding Constants of Candidate Antibodies to Human PD-L1 Recombinant Protein As shown in Table 1, the binding constants between different murine antibodies and human PD-L1 were determined by ForteBio instrument. The results showed that the murine antibodies 4, 6, 16, 17, 18 and 21 prepared in Example 5 were able to specifically bind to human PD-L1.

TABLE 1

| | Sample | | | | | |
|---|---|---|---|---|---|---|
| | 4 | 6 | 16 | 17 | 18 | 21 |
| KD (nM) | 1.7 | 0.1 | 0.5 | 1.6 | 2.3 | 0.9 |

Example 8. Acquisition of the Variable Region Sequences of the Candidate Antibodies Considering the expression level, activity, type, etc. of the antibodies expressed by the hybridoma cells, clones 6, 16, 18, 21 were selected for the subsequent experiments. Candidate hybridoma cells were cultured and collected by centrifugation at 1000 rpm, and total RNA was extracted with Trizol. After synthesizing the first strand cDNA using this as a template, the first strand cDNA was used as a subsequent template to amplify the variable region DNA sequence of the hybridoma cells. The primer sequences used in the amplification reaction were complementary to the variable region, the first framework region and constant region of the antibody (Larrick, J. W. et al., 1990, Scand. J. Immunol., 32, 121-128 and Coloma, J. J. et al., (1991) BioTechniques, 11, 152-156). In the 50 μl reaction system, the following substances were added: 1 μl of cDNA, 5 μl of 10×PCR buffer, 1 μl (25 pmol) of each of the upstream and downstream primers, 1 μl of dNTP, 1 μl of 25 mmol PL $MgCl_2$, 39 μl of $H_2O$. The pre-denaturation was carried out at 95° C. for 10 min. One microliter of Taq enzyme was added to enter the temperature cycle, and PCR amplification was performed. The reaction conditions were: denaturation at 94° C. for 1 min, annealing at 58° C. for 1 min, and extension at 72° C. for 15 s for a total of 32 cycles, followed by incubation at 72° C. for 10 min.

The consensus sequence was searched in the germline and rearranged Ig variable region sequence database using NCBI Ig-Blast (http://www.ncbi.nlm.nih.gov/projects/igblast/). Complementarity determining regions (CDRs) were identified based on Kabat (Wu, T. T and Kabat, E. A. 1970 J. Exp. Med., 132:211-250) and IMGT system (Lefranc M.-P. et al., 1999 Nucleic Acids Research, 27, 209-212) by sequence endorsement and by Internet-based sequence analysis (http://www.Imgt.org/IMGT_vquest/share/textes/index-.html and http://www.ncbi.nlm.nih.gov/igblast/).

The amino acid sequences of the light and heavy chain variable regions and CDRs encoded by the hybridoma cells are shown in the following table (corresponding to the sequences disclosed in the sequence listing):

The sequences of the candidate hybridoma heavy and light chain variable regions as shown below were obtained by sequencing the amplification products:

Clone 6:
Light chain: SEQ ID NO: 31;
LCDR1: SEQ ID NO: 1;
LCDR2: SEQ ID NO: 2;
LCDR3: SEQ ID NO: 3;
Light chain variant: SEQ ID NO: 32;
LCDR1: SEQ ID NO: 4;
LCDR2: SEQ ID NO: 5;
LCDR3: SEQ ID NO: 6;
Heavy chain: SEQ ID NO: 33;
HCDR1: SEQ ID NO: 7;
HCDR2: SEQ ID NO: 8;
HCDR3: SEQ ID NO: 9.
Clone 16:
Light chain: SEQ ID NO: 34;
LCDR1: SEQ ID NO: 10;
LCDR2: SEQ ID NO: 11;
LCDR3: SEQ ID NO: 12;
Heavy chain: SEQ ID NO: 35;
HCDR1: SEQ ID NO: 13;
HCDR2: SEQ ID NO: 14;
HCDR3: SEQ ID NO: 15.
Clone 18:
Light chain: SEQ ID NO: 36;
LCDR1: SEQ ID NO: 16;
LCDR2: SEQ ID NO: 17;
LCDR3: SEQ ID NO: 18;
Heavy chain: SEQ ID NO: 37;
HCDR1: SEQ ID NO: 19;
HCDR2: SEQ ID NO: 20;
HCDR3: SEQ ID NO: 21;
Heavy chain variant: SEQ ID NO: 38;
HCDR1: SEQ ID NO: 22;
HCDR2: SEQ ID NO: 23;
HCDR3: SEQ ID NO: 24.
Clone 21:
Light chain: SEQ ID NO: 39;
LCDR1: SEQ ID NO: 25;
LCDR2: SEQ ID NO: 26;
LCDR3: SEQ ID NO: 27;
Heavy chain: SEQ ID NO: 40;
HCDR1: SEQ ID NO: 28;
HCDR2: SEQ ID NO: 29;
HCDR3: SEQ ID NO: 30.

Example 9. Construction of Chimeric Antibody Expression Vector

The heavy chain constant region Fc fragment and the light chain k constant region were cloned from human blood cells (Beijing Institute of Hematology) and ligated into the pCDNA3.1 plasmid (see Walls M A, Hsiao H and Harris L J (1993), Nucleic Acids Research, Vol. 21, No. 122921-2929) for engineering. The fragments of the heavy and light chain variable region sequences of clones 6, 16, 18, 21 described in Example 8 were synthesized by Genscript. The heavy chain was digested with Bspq I and the light chain was digested with Bspq I before ligation into pCDNA3.1 plasmid that was correspondingly engineered. Sequencing was performed to determine the correct clone. Subsequent experimental materials were extracted and obtained from cells transfected with this series of plasmids.

Example 10. ELISA Detection of Binding of Chimeric Antibodies to Human PD-L1

A 96-well microtiter plate was coated with 0.5 µg/ml human PD-L1 and incubated at 37° C. for 60 minutes. The solution in the wells was then discarded, and the wells were washed 3 times with washing buffer, and blocked with PBS containing 2% BSA for 60 minutes. After washed 3 times with washing buffer, the wells were added with the gradiently diluted antibodies, incubated at 37° C. for 60 minutes, rinsed 3 times with washing buffer, then added with 1:10000 dilution of biotin-anti-IgG4 antibodies and incubated at 37° C. for 1 hour. After washed with washing buffer for 3 times, the wells were added with HPR-streptavidin diluted 1:10000 with washing buffer, incubated for 1 hour at room temperature, rinsed 3 times with washing buffer, and added with 100 µl of TMB substrate solution for development. After reacting for 30 minutes at room temperature, the reaction was terminated with 100 µl of 2 M hydrochloric acid solution and the absorbance was read at 450 nm.

Figure 6:
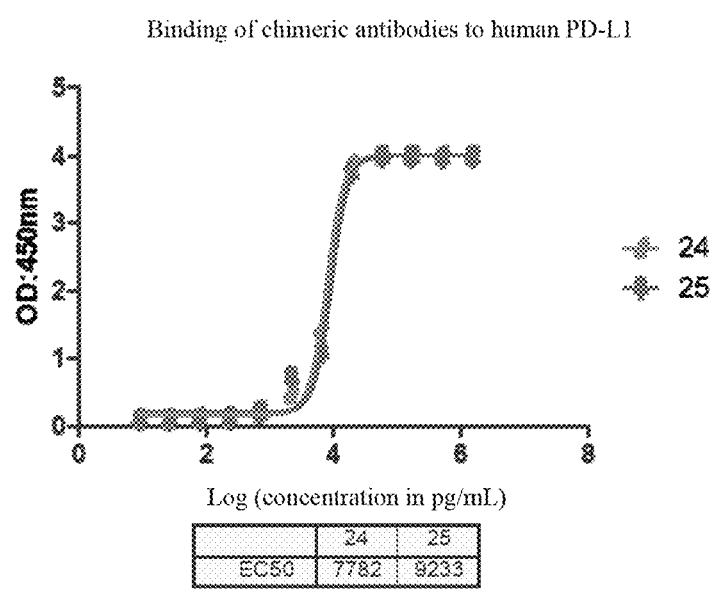
FIG. 6: Binding of chimeric antibodies to human PD-L1.

As can be seen from the results shown in FIG. 6, chimeric antibodies 24, 25 can specifically bind to PD-L1 with $EC_{50}$ values of 7.782 ng/mL and 9.233 ng/mL, respectively.

Example 11. Binding of Chimeric Antibodies to PD-L1 on 293F Cells

The 293F cells expressing PD-L1 were digested, resuspended in FACS buffer, added to a 1.5 ml EP tube at ~$2.5\times10^4$ cells in 50 µl volume, into which 50 µl of chimeric antibody dilution of different concentrations was added and mixed. The mixture was incubated at room temperature for 30 min. The cells were washed twice with FACS buffer, before adding 100 µl of goat anti-human IgG-PE antibody and incubation for 30 min in the dark. The cells were washed twice with FACS buffer and analyzed via FACS.

Figure 7:
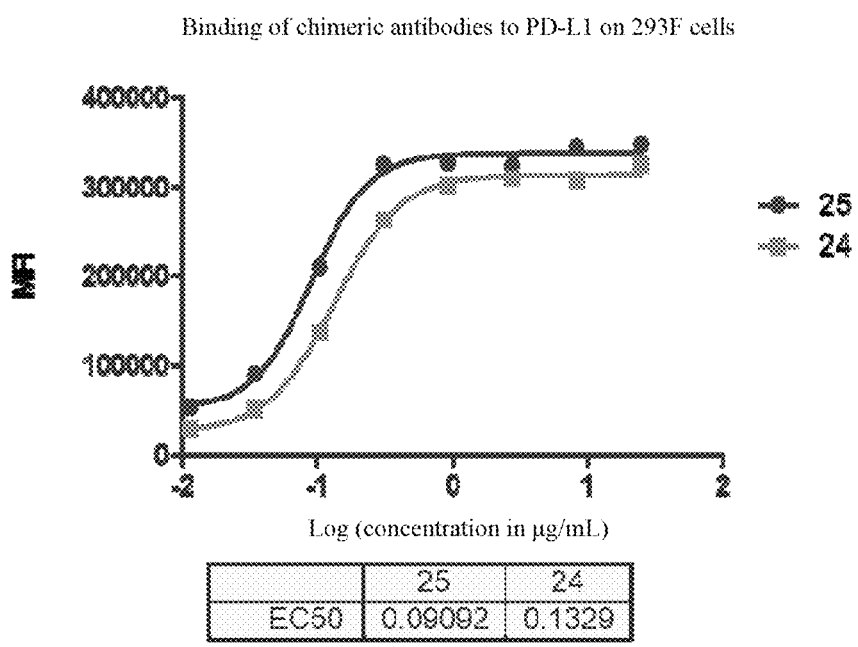
FIG. 7: Binding of chimeric antibodies to PD-L1 on 293F cells.

As a result, as shown in FIG. 7, chimeric antibodies 24, 25 can specifically bind to PD-L1 on 293F cells. The $EC_{50}$ values were 0.09092 µg/mL and 0.1329 µg/mL, respectively.

Example 12. Chimeric Antibody Inhibits Binding of Human PD-L1 to PD-1 on 293F Cells The recombinantly expressed chimeric antibody (10 µg/ml) was mixed with biotin-labeled human PD-L1 (i.e., human PD-L1 extracellular domain protein obtained in Example 1, at 1 µg/ml), and incubated at room temperature for 30 minutes. The mixture was then incubated with a suspension of 293F PD-1 stable cell strain ($1.5\times10^5$ cells) for 15 minutes at 37° C. The cells were eluted 3 times with PBS, contacted with 5 µg/ml of SA-APC and incubated for 30 minutes at room temperature. After eluting 3 times with PBS, the cells were analyzed by flow cytometry to verify whether the chimeric antibody can inhibit the binding of human PD-L1 to PD-1 on the surface of 293F cells.

Figure 8:
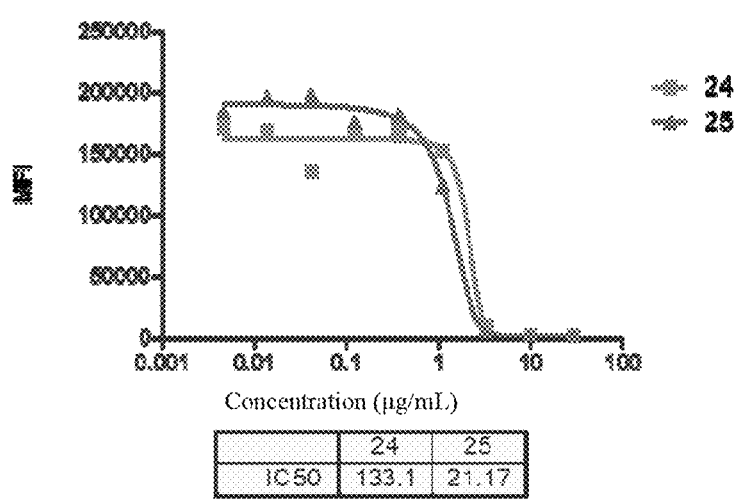
FIG. 8: Chimeric antibodies inhibit the binding of human PD-L1 to PD-1 on 293F cells.

As a result, as shown in FIG. 8, chimeric antibodies 24 and 25 can specifically inhibit the binding of human PD-L1 to PD-1 on the surface of 293F cells. The $IC_{50}$ values were 133.1 µg/mL and 21.17 µg/mL, respectively.

Example 13. Jurkat Fluorescein Analysis of Chimeric Antibodies

CHO cells expressing PD-L1 were plated into 96-well plates at $5\times10^4$ cells per well, incubated under 37° C. and 7% $CO_2$ overnight before the removal of cell supernatant. Forty microliter of antibody dilution was added to each well (starting concentration was 60 µg/ml, 3 fold concentration gradient dilution), and 40 µl of Jurkat reporter cells capable of continuously expressing PD-1 and NFAT-luciferase reporter gene was added (in a total cell number of $1\times10^5$ cells). The cells were cultured at 37° C., 7% $CO_2$ for 6 hours. Luciferase reagent was added and the luminescence value was detected by a microplate reader.

Figure 9:
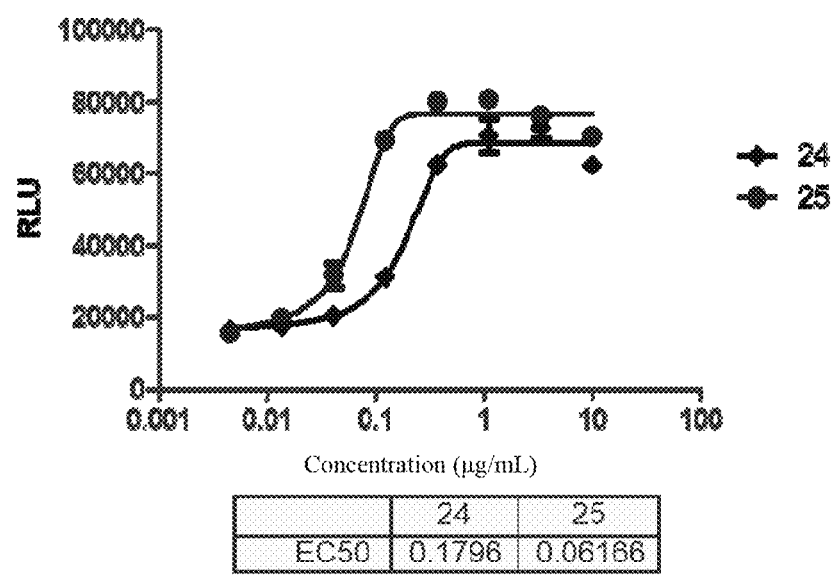
FIG. 9: Jurkat fluorescein analysis of chimeric antibodies.

As a result, as shown in FIG. 9, chimeric antibodies 24 and 25 can specifically inhibit the binding of human PD-L1 to PD-1 and promote the expression of the reporter gene. The $EC_{50}$ values were 0.1796 µg/mL and 0.06166 µg/mL, respectively.

Example 14. Humanization of the Antibodies

The humanized engineering was carried out to the variable region sequences of the antibodies secreted by the hybridoma cells obtained above. Briefly, the humanization process involves the following steps: A. aligning the gene sequence of the antibody secreted by each hybridoma cell with the human embryonic antibody gene sequence to find a sequence with high homology; B. Analyzing and investigating HLA-DR affinity, and selecting the human embryonic framework sequence with low affinity; C. analyzing the amino acid sequence of the variable region and its surrounding frame using computer simulation technology and molecular docking, and investigating the spatial stereoscopic binding mode thereof. By calculating electrostatic force, van der Waals force, hydrophilicity and entropy, the key amino acid individuals in the gene sequence of the antibody secreted by each hybridoma cell that can interact with PD-1 and maintain the spatial framework were analyzed and grafted back to the selected human embryonic gene framework, and based on this, the amino acid sites of the framework regions that must be retained for synthesis of humanized antibodies were identified (Pini, A. et al., (1998). Design and Use of a Phage Display Library: HUMAN ANTIBODIES WITH 10 SUBNANOMOLAR AFFINITY AGAINST A MARKER OF ANGIOGENESIS ELUTED FROM A TWO-DIMENSIONAL GEL., Journal of Biological Chemistry, 273(34): 21769-21776). On this basis we obtained the following 2 humanized antibodies 30 and 38:
Humanized antibody 30, light chain:
SEQ ID NO: 42, amino acid sequence of the light chain variable region;
SEQ ID NO: 43, nucleotide sequence of the light chain variable region;

Humanized antibody 30, heavy chain:
SEQ ID NO: 44, amino acid sequence of the heavy chain variable region;
SEQ ID NO: 45, nucleotide sequence of the heavy chain variable region.
Humanized antibody 38, light chain:
SEQ ID NO: 46, amino acid sequence of light chain variable region;
SEQ ID NO: 47, nucleotide sequence of the light chain variable region;
Humanized antibody 38, heavy chain:
SEQ ID NO: 48, amino acid sequence of the heavy chain variable region;
SEQ ID NO: 49, nucleotide sequence of the heavy chain variable region.

Example 15. ELISA Detection of Binding of Humanized Antibodies to Human PD-L1

A 96-well microtiter plate was plated, coated with PD-L1, and incubated at 37° C. for 60 minutes. The solution in the wells was then discarded, and the wells were washed 3 times with washing buffer, and blocked with PBS containing 2% BSA for 60 minutes. After washed 3 times with washing buffer, each well was added with 100 μl of biotin-labeled IgG4 antibody, incubated at 37° C. for 30 minutes, washed 3 times with washing buffer, then added with humanized antibodies of different dilutions, and incubated at 37° C. for 1 hour. After washed 3 times with washing buffer, the cells were incubated with HPR-labeled mouse anti-human IgG (H+L) (diluted 1:10000 with washing buffer) at room temperature for 1 hour, washed 3 times with washing buffer, and then added with 100 μl of TMB substrate for development. After reacting for 30 minutes at room temperature, the reaction was terminated with 100 μl of 2 M hydrochloric acid solution and the absorbance was read at 450 nm.

Figure 10:
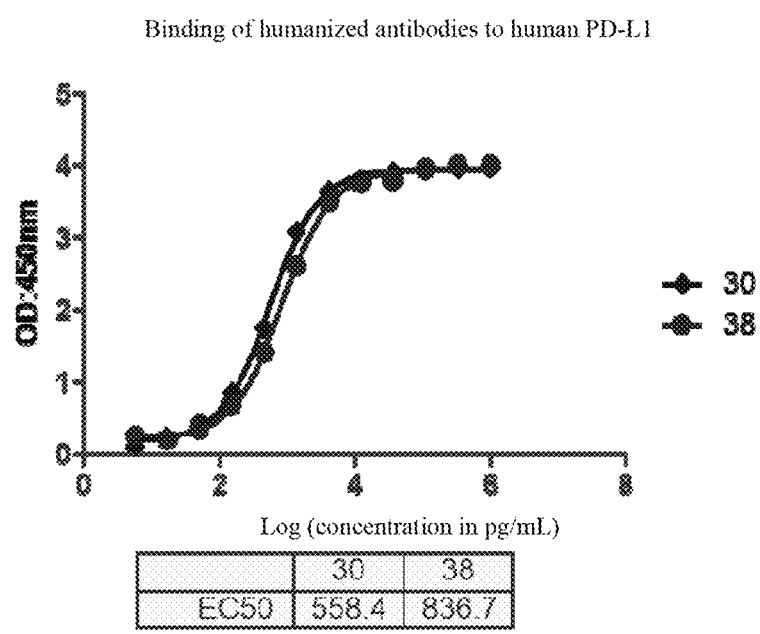
FIG. 10: Binding of humanized antibodies to human PD-L1.

As a result, as shown in FIG. 10, the $EC_{50}$ values for the binding of humanized antibodies 30 and 38 to PD-L1 were 558 pg/mL and 837 pg/mL, respectively.

Example 16. Binding of Humanized Antibodies to PD-L1 on 293F Cells

The 293F cells expressing PD-L1 were digested, resuspended in FACS buffer, and added to a 1.5 ml EP tube at ~2.5×10⁴ cells in 50 μl. Antibody (humanized antibodies 30, 38) dilutions at different concentrations was added in a volume of 50 μl, mixed and incubated at room temperature for 30 min. The cells were washed twice with FACS buffer, contacted with 100 μl of goat anti-human IgG-PE antibody, and incubated for 30 min in the dark. FACS was performed after washing twice with FACS buffer.

Figure 11:
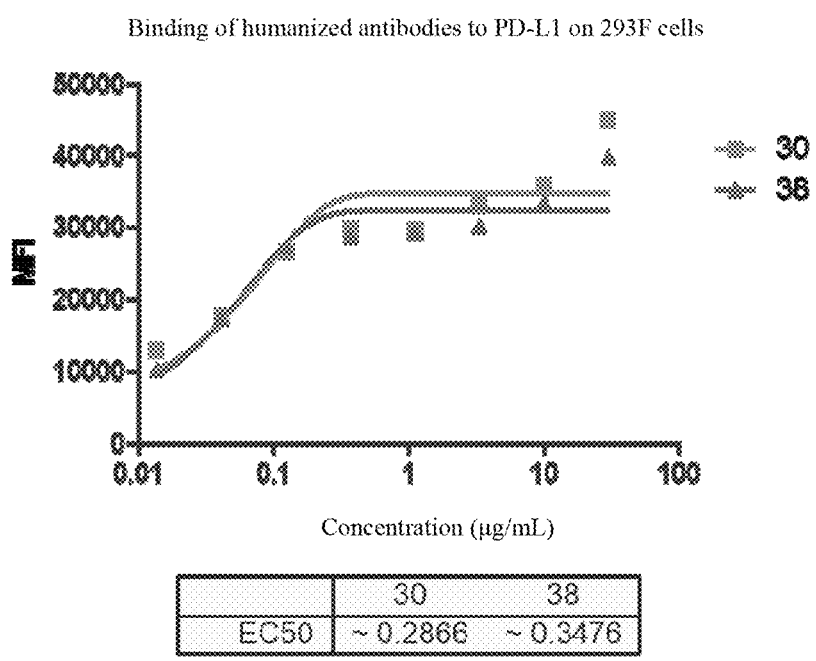
FIG. 11: Binding of humanized antibodies to PD-L1 on 293F cells.

As a result, as shown in FIG. 11, humanized antibodies 30, 38 can specifically bind to PD-L1 on 293F cells. The $EC_{50}$ values were 0.2866 μg/mL and 0.3476 μg/mL, respectively.

Example 17. Humanized Antibody Inhibits Binding of Human PD-L1 to PD-1 on 293F Cells The recombinantly expressed humanized antibody (10 μg/ml) was mixed with biotin-labeled human PD-L1 (i.e., human PD-L1 extracellular domain protein obtained in Example 1, at 1 μg/ml), and incubated at room temperature for 30 minutes. The mixture was then incubated with 293F PD-1 stable cell strain (1.5×10⁵ cells) for 15 minutes at 37° C., eluted 3 times with PBS, before adding 5 μg/ml of SA-APC and incubating for 15 minutes at 4° C. After eluting 3 times with PBS, the cells were analyzied by flow cytometry to verify whether the humanized antibodies can inhibit binding of human PD-L1 to PD-1 on the surface of 293F cells.

Figure 12:
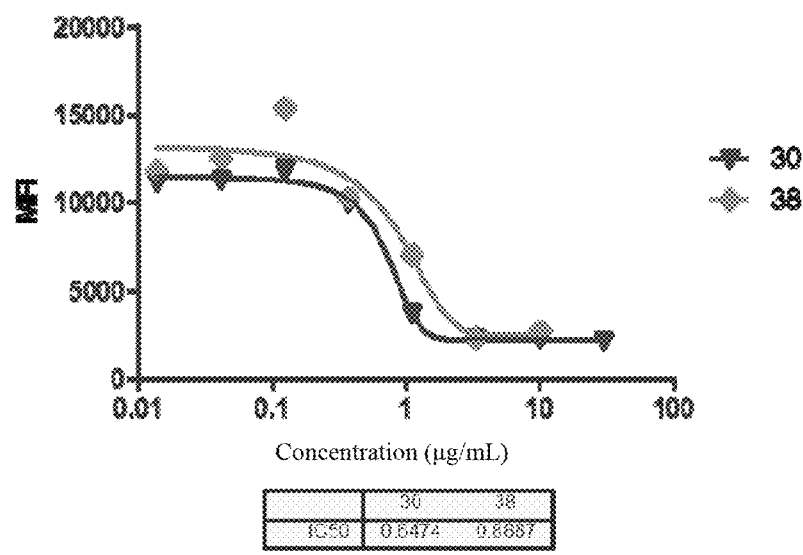
FIG. 12: Humanized antibodies inhibit the binding of human PD-L1 to PD-1 on 293F cells.

As a result, as shown in FIG. 12, humanized antibodies 30 and 38 can specifically inhibit binding of human PD-L1 to PD-1 on the surface of 293F cells. The $IC_{50}$ values were 0.6474 μg/mL and 0.8887 μg/mL, respectively.

Example 18. Jurkat Fluorescein Analysis of Humanized Antibodies

CHO cells expressing PD-L1 were plated into 96-well plates at 5×10⁴ per well, incubated at 37° C., 7% $CO_2$ overnight, and the cell supernatant was removed. To each well, 40 μl of antibody dilution was added (starting concentration was 60 μg/ml, 3 fold concentration gradient dilution), and 40 μl of Jurkat reporter cells capable of continuously expressing PD-1 and NFAT-luciferase reporter gene was added in a total cell number of 1×10⁵ cells, cultured at 37° C., 7% $CO_2$ for 6 hours. Luciferase reagent was added and the luminescence value was detected by a microplate reader.

Figure 13:
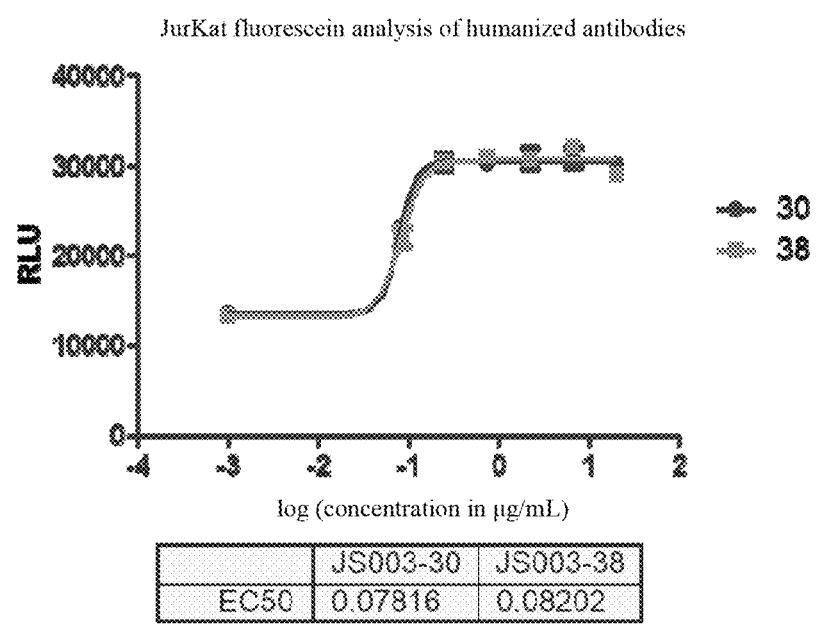
FIG. 13: Jurkat fluorescein analysis of humanized antibodies.

As a result, as shown in FIG. 13, humanized antibodies 30 and 38 can specifically inhibit the binding of human PD-L1 to PD-1 and promote the expression of the reporter gene. The $EC_{50}$ values were 0.07816 μg/mL and 0.08202 μg/mL, respectively.

Example 19. ELISA Assay Comparing the Binding of Humanized Antibodies to Human PD-L1

A 96-well microtiter plate was plated, coated with hPD-L1-his, and incubated at 37° C. for 90 minutes. The mixture was equilibrated at room temperature for about 5 minutes, washed with a plate washer, 300 μL/well*6 times, and incubated with PBS containing 2% BSA at 37° C. for 90 minutes. The plate was washed with a plate washer, 300 μL/well*6 times. The test solution was added 100 μl per well, incubate at 37° C. for 60 minutes, then the plate was washed with the plate washer, 300 μL/well*6 times, contacted with HPR-labeled anti-human IgG (FC-specific)-peroxidase antibody diluted at 1:5000 with diluting solution, incubated at 37° C. for 1 hour, washed by plate washer, 300 μL/well*6 times. TMB substrate solution (100 μl) was added for development. After reacting at 37° C. for 30 minutes, the reaction was stopped with 100 μl of 2 M hydrochloric acid solution and the absorbance was read at 450 nm.

Figure 14:
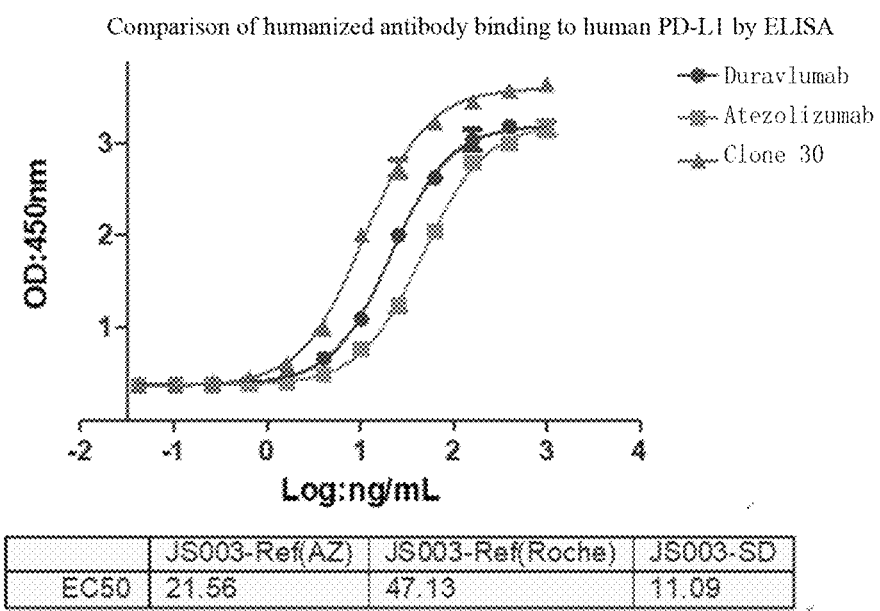
FIG. 14: Elisa assay comparing the binding of humanized antibodies to human PD-L1.

As a result, as shown in FIG. 14, the $EC_{50}$ value for the binding of humanized antibody 30 to human PD-L1 was 11.09 ng/mL, the $EC_{50}$ value of durvaluma was 21.56 ng/mL, and the $EC_{50}$ value for atezolizumab was 47.13 ng/mL.

Example 20 Inhibition of Mouse Tumor Growth by Humanized Antibodies

Fifteen female C57BL/6J mice, 6-8 weeks old, were injected with 1×10⁶ (50 μL) MC38-B7H1 colon cancer cells to the right axilla, and after the tumor was formed on the $5^{th}$-$7^{th}$ day, the tumor volumes in the mice were measured. The mice were divided into 3 groups, 5 in each group. Group 1 was intraperitoneally injected with 100 μL of KLH; Group 2 was intraperitoneally injected with 150 μg/100 μL of antibody 30; and Group 3 was injected intraperitoneally with 150 µg/100 µL of antibody 38. Injections were given twice a week for 3 weeks. Tumor volumes were measured 3 times per week and calculated as length×width/2.

Figure 15:
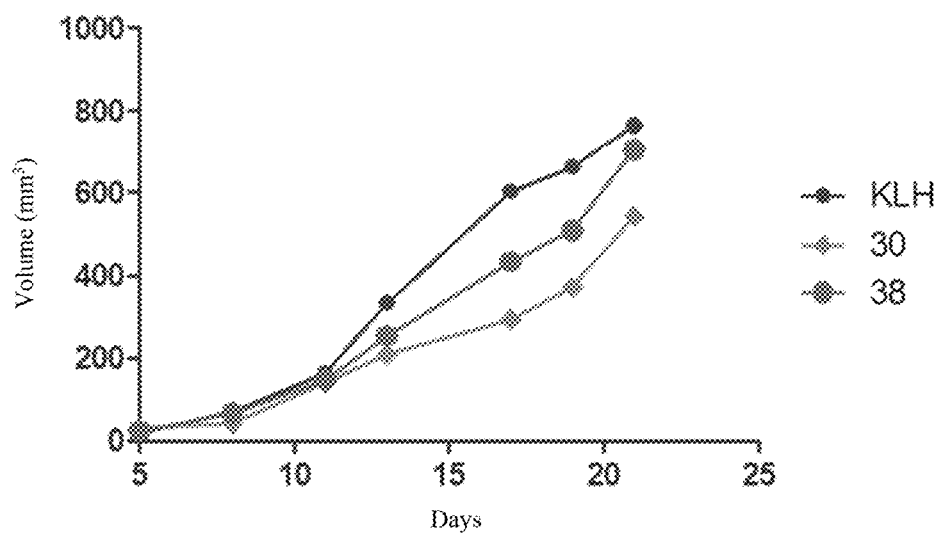
FIG. 15: In vivo assay detecting the inhibition of tumor growth by humanized antibodies.

As a result, as shown in FIG. 15, humanized antibodies 30 and 38 can significantly inhibit the growth of MC38-B7H1-induced tumors.

The invention claimed is:

1. An antibody or a functional fragment thereof capable of specifically binding to human PD-L1, wherein:

the antibody or a functional fragment thereof comprises LCDR1 consisting of the amino acid sequence of SEQ ID NO:1, LCDR2 consisting of the amino acid sequence of SEQ ID NO:2, LCDR3 consisting of the amino acid sequence of SEQ ID NO:3, HCDR1 consisting of the amino acid sequence of SEQ ID NO:7, HCDR2 consisting of the amino acid sequence of SEQ ID NO:8 and HCDR3 consisting of the amino acid sequence of SEQ ID NO:9; or the antibody or a functional fragment thereof comprises LCDR1 consisting of the amino acid sequence of SEQ ID NO:4, LCDR2 consisting of the amino acid sequence of SEQ ID NO:5, LCDR3 consisting of the amino acid sequence of SEQ ID NO:6, HCDR1 consisting of the amino acid sequence of SEQ ID NO:7, HCDR2 consisting of the amino acid sequence of SEQ ID NO:8 and HCDR3 consisting of the amino acid sequence of SEQ ID NO:9; or the antibody or a functional fragment thereof comprises LCDR1 consisting of the amino acid sequence of SEQ ID NO:10, LCDR2 consisting of the amino acid sequence of SEQ ID NO:11, LCDR3 consisting of the amino acid sequence of SEQ ID NO:12, HCDR1 consisting of the amino acid sequence of SEQ ID NO:13, HCDR2 consisting of the amino acid sequence of SEQ ID NO:14 and HCDR3 consisting of the amino acid sequence of SEQ ID NO:15; or the antibody or a functional fragment thereof comprises LCDR1 consisting of the amino acid sequence of SEQ ID NO:16, LCDR2 consisting of the amino acid sequence of SEQ ID NO:17, LCDR3 consisting of the amino acid sequence of SEQ ID NO:18, HCDR1 consisting of the amino acid sequence of SEQ ID NO:19, HCDR2 consisting of the amino acid sequence of SEQ ID NO:20 and HCDR3 consisting of the amino acid sequence of SEQ ID NO:21; or the antibody or a functional fragment thereof comprises LCDR1 consisting of the amino acid sequence of SEQ ID NO:16, LCDR2 consisting of the amino acid sequence of SEQ ID NO:17, LCDR3 consisting of the amino acid sequence of SEQ ID NO:18, HCDR1 consisting of the amino acid sequence of SEQ ID NO:22, HCDR2 consisting of the amino acid sequence of SEQ ID NO:23 and HCDR3 consisting of the amino acid sequence of SEQ ID NO:24; or the antibody or a functional fragment thereof comprises LCDR1 consisting of the amino acid sequence of SEQ ID NO:25, LCDR2 consisting of the amino acid sequence of SEQ ID NO:26, LCDR3 consisting of the amino acid sequence of SEQ ID NO:27, HCDR1 consisting of the amino acid sequence of SEQ ID NO:28, HCDR2 consisting of the amino acid sequence of SEQ ID NO:29 and HCDR3 consisting of the amino acid sequence of SEQ ID NO:30.

2. The antibody or a functional fragment thereof according to claim 1, comprising a heavy chain variable region having an amino acid sequence selected from the group consisting of SEQ ID NOs: 33, 35, 37, 38, and 40, and/or a light chain variable region having an amino acid sequence selected from the group consisting of SEQ ID NOs: 31, 32, 34, 36, and 39.

3. The antibody or a functional fragment thereof according to claim 2, wherein the heavy chain variable region is set forth in SEQ ID NO: 33 and the light chain variable region is set forth in SEQ ID NO: 31, or the heavy chain variable region is set forth in SEQ ID NO: 33 and the light chain variable region is set forth in SEQ ID NO: 32, or the heavy chain variable region is set forth in SEQ ID NO: 35 and the light chain variable region is set forth in SEQ ID NO: 34, or the heavy chain variable region is set forth in SEQ ID NO: 37 and the light chain variable region is set forth in SEQ ID NO: 36, or the heavy chain variable region is set forth in SEQ ID NO: 38 and the light chain variable region is set forth in SEQ ID NO: 36, or the heavy chain variable region is set forth in SEQ ID NO: 40 and the light chain variable region is set forth in SEQ ID NO: 39.

4. The antibody or a functional fragment thereof according to claim 1, which is a chimeric antibody or a humanized antibody.

5. The antibody or a functional fragment thereof according to claim 1, comprising a heavy chain variable region having an amino acid sequence selected from the group consisting of SEQ ID NO: 44 and SEQ ID NO: 48, and a light chain variable region having an amino acid sequence selected from the group consisting of SEQ ID NO: 42 and SEQ ID NO: 46.

6. The antibody or a functional fragment thereof according to claim 1, wherein the antibody comprising:
a heavy chain variable region having an amino acid sequence SEQ ID NO: 48, and a light chain variable region having an amino acid sequence SEQ ID NO: 46; or
a heavy chain variable region having an amino acid sequence SEQ ID NO: 44, and a light chain variable region having an amino acid sequence SEQ ID NO: 42.

7. A pharmaceutical composition comprising the antibody or a functional fragment thereof according to claim 1, and a pharmaceutically acceptable carrier.

8. An immunoconjugate comprising the antibody or a functional fragment thereof according to claim 1 conjugated with a therapeutic agent.

9. The immunoconjugate according to claim 8, wherein the therapeutic agent is a toxin, a radioisotope, a drug or a cytotoxic agent.

10. An isolated nucleic acid molecule encoding the antibody or a functional fragment thereof according to claim 1.

11. An isolated nucleic acid molecule encoding the amino acid sequence set forth in any of SEQ ID NOs: 31-40, 42, 44, 46 and 48.

12. An expression vector or a host cell comprising a nucleic acid molecule encoding the antibody or a functional fragment thereof according to claim 1.

13. An expression vector or host cell comprising the nucleic acid molecule according to claim 11.

14. A pharmaceutical composition comprising an isolated nucleic acid molecule encoding the antibody or a functional fragment thereof according to claim 1, and a pharmaceutically acceptable carrier.

15. A method for treating a cancer caused by T cell dysfunction by eliminating, inhibiting or reducing PD-L1 activity, comprising administering to a subject in need thereof an effective amount of the antibody or a functional fragment thereof according to claim 1, or a pharmaceutical composition comprising the antibody or a functional fragment thereof.

16. The method according to claim 15, wherein the cancer is a breast cancer, lung cancer, head and neck cancer, prostate cancer, esophageal cancer, tracheal cancer, skin cancer, brain cancer, liver cancer, bladder cancer, stomach cancer, pancreatic cancer, ovarian cancer, uterine cancer, cervical cancer, testicular cancer, colon cancer or rectal cancer.

17. A method for enhancing T cell function to upregulate a cell-mediated immune response by eliminating, inhibiting or reducing PD-L1 activity, comprising administering to a subject in need thereof an effective amount of the antibody or a functional fragment thereof according to claim 1, or a pharmaceutical composition comprising the antibody or a functional fragment thereof.

* * * * *

```
                        SEQUENCE LISTING

<160> NUMBER OF SEQ ID NOS: 51

<210> SEQ ID NO 1
<211> LENGTH: 6
<212> TYPE: PRT
<213> ORGANISM: Artificial sequence
<220> FEATURE:
<223> OTHER INFORMATION: Synthetic LCDR1

<400> SEQUENCE: 1

Lys Ser Ile Ser Lys Tyr
1               5

<210> SEQ ID NO 2
<211> LENGTH: 3
<212> TYPE: PRT
<213> ORGANISM: Artificial sequence
<220> FEATURE:
<223> OTHER INFORMATION: Synthetic LCDR2

<400> SEQUENCE: 2

Ser Gly Ser
1

<210> SEQ ID NO 3
<211> LENGTH: 9
<212> TYPE: PRT
<213> ORGANISM: Artificial sequence
<220> FEATURE:
<223> OTHER INFORMATION: Synthetic LCDR3

<400> SEQUENCE: 3

Gln Gln His Tyr Glu Glu Pro Trp Thr
1               5

<210> SEQ ID NO 4
<211> LENGTH: 6
<212> TYPE: PRT
<213> ORGANISM: Artificial sequence
<220> FEATURE:
<223> OTHER INFORMATION: Synthetic LCDR1

<400> SEQUENCE: 4

Gln Asp Val Ser His Gly
1               5

<210> SEQ ID NO 5
<211> LENGTH: 3
<212> TYPE: PRT
<213> ORGANISM: Artificial sequence
<220> FEATURE:
<223> OTHER INFORMATION: Synthetic LCDR2

<400> SEQUENCE: 5

Trp Ala Ser
1

<210> SEQ ID NO 6
<211> LENGTH: 9
<212> TYPE: PRT
<213> ORGANISM: Artificial sequence
<220> FEATURE:
<223> OTHER INFORMATION: Synthetic LCDR3
```

<400> SEQUENCE: 6

Gln Gln His Tyr Ser Thr Pro Pro Thr
1               5

<210> SEQ ID NO 7
<211> LENGTH: 8
<212> TYPE: PRT
<213> ORGANISM: Artificial sequence
<220> FEATURE:
<223> OTHER INFORMATION: Synthetic HCDR1

<400> SEQUENCE: 7

Gly Asp Ser Phe Thr Ser Gly Tyr
1               5

<210> SEQ ID NO 8
<211> LENGTH: 7
<212> TYPE: PRT
<213> ORGANISM: Artificial sequence
<220> FEATURE:
<223> OTHER INFORMATION: Synthetic HCDR2

<400> SEQUENCE: 8

Ile Ser Tyr Thr Gly Ser Tyr
1               5

<210> SEQ ID NO 9
<211> LENGTH: 12
<212> TYPE: PRT
<213> ORGANISM: Artificial sequence
<220> FEATURE:
<223> OTHER INFORMATION: Synthetic HCDR3

<400> SEQUENCE: 9

Ala Arg Gly Leu Asn Trp Asp Glu Lys Phe Ala Tyr
1               5                   10

<210> SEQ ID NO 10
<211> LENGTH: 10
<212> TYPE: PRT
<213> ORGANISM: Artificial sequence
<220> FEATURE:
<223> OTHER INFORMATION: Synthetic LCDR1

<400> SEQUENCE: 10

Glu Ser Val Glu Phe Tyr Gly Thr Ser Leu
1               5                   10

<210> SEQ ID NO 11
<211> LENGTH: 3
<212> TYPE: PRT
<213> ORGANISM: Artificial sequence
<220> FEATURE:
<223> OTHER INFORMATION: Synthetic LCDR2

<400> SEQUENCE: 11

Ala Ala Ser
1

<210> SEQ ID NO 12
<211> LENGTH: 9
<212> TYPE: PRT
<213> ORGANISM: Artificial sequence
<220> FEATURE:
<223> OTHER INFORMATION: Synthetic LCDR3

```
<400> SEQUENCE: 12

Gln Gln Gly Arg His Val Pro Tyr Thr
1               5

<210> SEQ ID NO 13
<211> LENGTH: 8
<212> TYPE: PRT
<213> ORGANISM: Artificial sequence
<220> FEATURE:
<223> OTHER INFORMATION: Synthetic HCDR1

<400> SEQUENCE: 13

Gly Tyr Thr Phe Thr Asn Tyr Val
1               5

<210> SEQ ID NO 14
<211> LENGTH: 8
<212> TYPE: PRT
<213> ORGANISM: Artificial sequence
<220> FEATURE:
<223> OTHER INFORMATION: Synthetic HCDR2

<400> SEQUENCE: 14

Ile Asn Pro Asn Ile Asp Gly Gly
1               5

<210> SEQ ID NO 15
<211> LENGTH: 6
<212> TYPE: PRT
<213> ORGANISM: Artificial sequence
<220> FEATURE:
<223> OTHER INFORMATION: Synthetic HCDR3

<400> SEQUENCE: 15

Ala Lys Pro Arg Gly Ser
1               5

<210> SEQ ID NO 16
<211> LENGTH: 11
<212> TYPE: PRT
<213> ORGANISM: Artificial sequence
<220> FEATURE:
<223> OTHER INFORMATION: Synthetic LCDR1

<400> SEQUENCE: 16

Ser Leu Leu Tyr Ser Asn Tyr Gln Lys His Ser
1               5                   10

<210> SEQ ID NO 17
<211> LENGTH: 3
<212> TYPE: PRT
<213> ORGANISM: Artificial sequence
<220> FEATURE:
<223> OTHER INFORMATION: Synthetic LCDR2

<400> SEQUENCE: 17

Trp Ala Ser
1

<210> SEQ ID NO 18
<211> LENGTH: 9
<212> TYPE: PRT
<213> ORGANISM: Artificial sequence
<220> FEATURE:
<223> OTHER INFORMATION: Synthetic LCDR3

<400> SEQUENCE: 18
```

```
Gln Gln Tyr Tyr Ser Tyr Pro Phe Thr
1               5

<210> SEQ ID NO 19
<211> LENGTH: 8
<212> TYPE: PRT
<213> ORGANISM: Artificial sequence
<220> FEATURE:
<223> OTHER INFORMATION: Synthetic HCDR1

<400> SEQUENCE: 19

Gly Asp Ser Phe Thr Ser Gly Tyr
1               5

<210> SEQ ID NO 20
<211> LENGTH: 7
<212> TYPE: PRT
<213> ORGANISM: Artificial sequence
<220> FEATURE:
<223> OTHER INFORMATION: Synthetic HCDR2

<400> SEQUENCE: 20

Ile Ser Tyr Ser Gly Ser Thr
1               5

<210> SEQ ID NO 21
<211> LENGTH: 12
<212> TYPE: PRT
<213> ORGANISM: Artificial sequence
<220> FEATURE:
<223> OTHER INFORMATION: Synthetic HCDR3

<400> SEQUENCE: 21

Ala Arg Cys Gly Gly Trp Leu Leu Pro Phe Thr Tyr
1               5                   10

<210> SEQ ID NO 22
<211> LENGTH: 8
<212> TYPE: PRT
<213> ORGANISM: Artificial sequence
<220> FEATURE:
<223> OTHER INFORMATION: Synthetic HCDR1

<400> SEQUENCE: 22

Gly Asp Ser Ile Thr Ser Gly Tyr
1               5

<210> SEQ ID NO 23
<211> LENGTH: 6
<212> TYPE: PRT
<213> ORGANISM: Artificial sequence
<220> FEATURE:
<223> OTHER INFORMATION: Synthetic HCDR2

<400> SEQUENCE: 23

Ser Tyr Thr Gly Ser Thr
1               5

<210> SEQ ID NO 24
<211> LENGTH: 12
<212> TYPE: PRT
<213> ORGANISM: Artificial sequence
<220> FEATURE:
<223> OTHER INFORMATION: Synthetic HCDR3

<400> SEQUENCE: 24
```

```
Ala Arg Gln Ala Gly Trp Leu Ile Ser Phe Asp Phe
1               5                   10
```

<210> SEQ ID NO 25
<211> LENGTH: 6
<212> TYPE: PRT
<213> ORGANISM: Artificial sequence
<220> FEATURE:
<223> OTHER INFORMATION: Synthetic LCDR1

<400> SEQUENCE: 25

```
Gln Asn Val Asp Thr Ser
1               5
```

<210> SEQ ID NO 26
<211> LENGTH: 3
<212> TYPE: PRT
<213> ORGANISM: Artificial sequence
<220> FEATURE:
<223> OTHER INFORMATION: Synthetic LCDR2

<400> SEQUENCE: 26

```
Ser Ala Ser
1
```

<210> SEQ ID NO 27
<211> LENGTH: 9
<212> TYPE: PRT
<213> ORGANISM: Artificial sequence
<220> FEATURE:
<223> OTHER INFORMATION: Synthetic LCDR3

<400> SEQUENCE: 27

```
Gln Gln Tyr Tyr Gly Tyr Pro Phe Thr
1               5
```

<210> SEQ ID NO 28
<211> LENGTH: 8
<212> TYPE: PRT
<213> ORGANISM: Artificial sequence
<220> FEATURE:
<223> OTHER INFORMATION: Synthetic HCDR1

<400> SEQUENCE: 28

```
Gly Asp Ser Ile Thr Arg Gly Tyr
1               5
```

<210> SEQ ID NO 29
<211> LENGTH: 7
<212> TYPE: PRT
<213> ORGANISM: Artificial sequence
<220> FEATURE:
<223> OTHER INFORMATION: Synthetic HCDR2

<400> SEQUENCE: 29

```
Ile Ser Tyr Thr Gly Ser Thr
1               5
```

<210> SEQ ID NO 30
<211> LENGTH: 12
<212> TYPE: PRT
<213> ORGANISM: Artificial sequence
<220> FEATURE:
<223> OTHER INFORMATION: Synthetic HCDR3

<400> SEQUENCE: 30

```
Ala Thr Ser Thr Gly Trp Leu Asp Pro Val Asp Tyr
```

```
1               5                    10
```

<210> SEQ ID NO 31
<211> LENGTH: 107
<212> TYPE: PRT
<213> ORGANISM: Artificial sequence
<220> FEATURE:
<223> OTHER INFORMATION: Synthetic Light chain variable region

<400> SEQUENCE: 31

```
Asp Val Gln Ile Thr Gln Ser Pro Phe Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Arg Gly Lys Asn Asn Lys Val Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Tyr Glu Gly Pro Trp
                85                  90                  95

Thr Phe Gly Gly Gly Thr Lys Leu Glu Ile Lys
            100                 105
```

<210> SEQ ID NO 32
<211> LENGTH: 107
<212> TYPE: PRT
<213> ORGANISM: Artificial sequence
<220> FEATURE:
<223> OTHER INFORMATION: Synthetic Light chain variable region

<400> SEQUENCE: 32

```
Asp Ile Val Met Thr Gln Ser His Lys Phe Val Ser Thr Ser Val Gly
1               5                   10                  15

Asp Arg Val Ser Ile Thr Cys Lys Ala Ser Gln Asp Val Ser His Gly
            20                  25                  30

Val Ala Trp Tyr Gln Gln Lys Pro Gly Gln Ser Pro Lys Val Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Ser Thr Pro Pro
                85                  90                  95

Thr Phe Gly Gly Gly Thr Lys Leu Glu Ile Lys
            100                 105
```

<210> SEQ ID NO 33
<211> LENGTH: 118
<212> TYPE: PRT
<213> ORGANISM: Artificial sequence
<220> FEATURE:
<223> OTHER INFORMATION: Synthetic Heavy chain variable region

<400> SEQUENCE: 33

```
Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Phe Thr Ser Gly
            20                  25                  30
```

Tyr Trp Asn Trp Ile Arg Lys Phe Pro Gly Asn Lys Phe Glu Tyr Met
          35                  40                  45

Gly Tyr Ile Ser Tyr Thr Gly Ser Tyr Tyr Phe Asn Pro Ser Leu Lys
 50                  55                  60

Ser Arg Ile Ser Ile Thr Arg Asp Thr Ser Lys Asn Gln Phe Tyr Leu
 65                  70                  75                  80

Gln Leu Asn Ser Val Thr Thr Glu Asp Thr Ala Thr Tyr Tyr Cys Ala
              85                  90                  95

Arg Gly Leu Asn Trp Asp Glu Lys Phe Ala Tyr Trp Gly Gln Gly Thr
             100                 105                 110

Leu Val Thr Val Ser Ala
             115

<210> SEQ ID NO 34
<211> LENGTH: 111
<212> TYPE: PRT
<213> ORGANISM: Artificial sequence
<220> FEATURE:
<223> OTHER INFORMATION: Synthetic Light chain variable region

<400> SEQUENCE: 34

Asp Ile Val Leu Thr Gln Ser Pro Ala Ser Leu Ala Val Ser Leu Gly
 1               5                  10                  15

Gln Arg Ala Thr Ile Ser Cys Arg Ala Ser Glu Ser Val Glu Phe Tyr
             20                  25                  30

Gly Thr Ser Leu Met Gln Trp Tyr Gln Gln Lys Pro Gly Gln Pro Pro
          35                  40                  45

Lys Leu Leu Ile Tyr Ala Ala Ser Asn Val Asp Ser Gly Val Pro Ala
 50                  55                  60

Arg Phe Ser Gly Ser Gly Ser Gly Thr Asp Phe Ser Leu Asn Ile His
 65                  70                  75                  80

Pro Val Glu Glu Asp Asp Ile Ala Met Tyr Phe Cys Gln Gln Gly Arg
              85                  90                  95

His Val Pro Tyr Thr Phe Gly Gly Gly Thr Lys Leu Glu Ile Lys
             100                 105                 110

<210> SEQ ID NO 35
<211> LENGTH: 113
<212> TYPE: PRT
<213> ORGANISM: Artificial sequence
<220> FEATURE:
<223> OTHER INFORMATION: Synthetic Heavy chain variable region

<400> SEQUENCE: 35

Glu Val Gln Leu Gln Gln Ser Gly Pro Glu Leu Val Lys Pro Gly Ala
 1               5                  10                  15

Ser Val Lys Met Ser Cys Lys Ala Ser Gly Tyr Thr Phe Thr Asn Tyr
             20                  25                  30

Val Ile His Trp Val Lys Gln Thr Pro Gly Gln Gly Leu Glu Trp Ile
          35                  40                  45

Gly Tyr Ile Asn Pro Asn Ile Asp Gly Gly Ser Tyr Asn Glu Lys Phe
 50                  55                  60

Asn Gly Lys Ala Lys Met Thr Ser Asp Lys Ser Ser Thr Val His
 65                  70                  75                  80

Met Glu Leu Arg Ser Leu Thr Tyr Glu Asp Phe Ala Val Tyr Tyr Cys
              85                  90                  95

Ala Lys Pro Arg Gly Ser Trp Gly Gln Gly Thr Leu Val Thr Val Ser

Ala

<210> SEQ ID NO 36
<211> LENGTH: 113
<212> TYPE: PRT
<213> ORGANISM: Artificial sequence
<220> FEATURE:
<223> OTHER INFORMATION: Synthetic Light chain variable region

<400> SEQUENCE: 36

```
Asp Ile Val Met Ser Gln Ser Pro Ser Leu Ala Val Ser Val Gly
1               5                   10                  15

Glu Lys Val Ala Met Ile Cys Lys Ser Ser Gln Ser Leu Leu Tyr Ser
            20                  25                  30

Asn Tyr Gln Lys His Ser Leu Ala Trp Tyr Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Phe Thr Phe Gly Ala Gly Thr Lys Leu Glu Leu
            100                 105                 110

Lys
```

<210> SEQ ID NO 37
<211> LENGTH: 118
<212> TYPE: PRT
<213> ORGANISM: Artificial sequence
<220> FEATURE:
<223> OTHER INFORMATION: Synthetic Heavy chain variable region

<400> SEQUENCE: 37

```
Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Phe Thr Ser Gly
            20                  25                  30

Tyr Trp Thr Trp Ile Arg Asn Phe Pro Gly Asn Lys Leu Asp Tyr Met
        35                  40                  45

Gly Tyr Ile Ser Tyr Ser Gly Ser Thr Tyr Tyr Asn Pro Ser Leu Lys
    50                  55                  60

Ser Arg Ile Ser Ile Thr Arg Asp Thr Ser Lys Asn Gln Phe Tyr Leu
65                  70                  75                  80

His Leu Asn Ser Val Thr Thr Glu Asp Thr Ala Thr Tyr Tyr Cys Ala
                85                  90                  95

Arg Cys Gly Gly Trp Leu Leu Pro Phe Thr Tyr Trp Gly Gln Gly Thr
            100                 105                 110

Leu Val Thr Val Ser Ala
        115
```

<210> SEQ ID NO 38
<211> LENGTH: 118
<212> TYPE: PRT
<213> ORGANISM: Artificial sequence
<220> FEATURE:
<223> OTHER INFORMATION: Synthetic Heavy chain variable region

<400> SEQUENCE: 38

Glu Val Gln Leu Gln Glu Ser Gly Pro Ser Leu Val Lys Leu Ser Gln
1               5                   10                  15

Thr Leu Ser Leu Thr Cys Ser Val Thr Gly Asp Ser Ile Thr Ser Gly
            20                  25                  30

Tyr Trp Asn Trp Ile Arg Lys Phe Pro Gly Asn Arg Leu Glu Asp Met
        35                  40                  45

Gly Tyr Ile Ser Tyr Thr Gly Ser Thr Tyr Asn Pro Ser Leu Lys
50                  55                  60

Ser Gly Ile Ser Ile Thr Arg Asp Pro Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg Gln Ala Gly Trp Leu Ile Ser Phe Asp Phe Trp Gly Gln Gly Thr
            100                 105                 110

Leu Val Thr Val Ser Ala
            115

<210> SEQ ID NO 39
<211> LENGTH: 107
<212> TYPE: PRT
<213> ORGANISM: Artificial sequence
<220> FEATURE:
<223> OTHER INFORMATION: Synthetic Light chain variable region

<400> SEQUENCE: 39

Asp Ile Val Met Thr Gln Ser Arg Lys Phe Met Ser Thr Ser Val Gly
1               5                   10                  15

Asp Arg Ala Ser Val Thr Cys Lys Ala Ser Gln Asn Val Asp Thr Ser
            20                  25                  30

Val Ala Trp Phe Gln Gln Lys Pro Gly Gln Ser Pro Lys Ala Leu Ile
        35                  40                  45

Tyr Ser Ala Ser Phe Arg Tyr Ser Gly Val Pro Asp Arg Phe Thr Gly
50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Tyr Gly Tyr Pro Phe
                85                  90                  95

Thr Phe Gly Ser Gly Thr Lys Leu Glu Ile Lys
            100                 105

<210> SEQ ID NO 40
<211> LENGTH: 118
<212> TYPE: PRT
<213> ORGANISM: Artificial sequence
<220> FEATURE:
<223> OTHER INFORMATION: Synthetic Heavy chain variable region

<400> SEQUENCE: 40

Glu Gly Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Arg Gly
            20                  25                  30

Tyr Trp Asn Trp Ile Arg Lys Phe Pro Gly Asn Lys Phe Glu Tyr Met
        35                  40                  45

Gly Tyr Ile Ser Tyr Thr Gly Ser Thr Tyr Ser Asn Leu Ser Leu Lys
50                  55                  60

Ser Arg Ile Ser Ile Thr Arg Asp Thr Ser Lys Asn His Tyr Tyr Leu
65                  70                  75                  80

Arg Leu Asn Ser Val Thr Thr Glu Asp Thr Ala Thr Tyr Tyr Cys Ala
                85                  90                  95

Thr Ser Thr Gly Trp Leu Asp Pro Val Asp Tyr Trp Gly Gln Gly Thr
            100                 105                 110

Leu Val Thr Val Ser Ala
        115

<210> SEQ ID NO 41
<211> LENGTH: 710
<212> TYPE: DNA
<213> ORGANISM: Artificial sequence
<220> FEATURE:
<223> OTHER INFORMATION: Synthetic Human PD-L1 extracellular fragment

<400> SEQUENCE: 41
atgaggatat ttgctgtctt tatattcatg acctactggc atttgctgaa cgcatttact     60
gtcacggttc ccaaggacct atatgtggta gagtatggta gcaatatgac aattgaatgc    120
aaattcccag tagaaaaaca attagacctg gctgcactaa ttgtctattg ggaaatggag    180
gataagaaca ttattcaatt tgtgcatgga tgaaggttca gcatagtagc tacagacaga    240
gggcccggct gttgaaggac cagctctccc tgggaaatgc tgcacttcag atcacagatg    300
tgaaattgca ggatgcaggg gtgtaccgct gcatgatcag ctatggtggt gccgactaca    360
agcgaattac tgtgaaagtc aatgccccat acaacaaaat caaccaaaga attttggttg    420
tggatccagt cacctctgaa catgaactga catgtcaggc tgagggctac ccaaggccg     480 aagtcatctg acaagcagt gaccatcaag tcctgagtgg taagaccacc accaccaatt    540
ccaagagaga ggagaagctt ttcaatgtga ccagcacact gagaatcaac acaacaacta    600
atgagatttt ctactgcact tttaggagat tagatcctga ggaaaaccat acagctgaat    660
tggtcatccc agaactacct ctggcacatc ctccaaatga aaggactcac                710

<210> SEQ ID NO 42
<211> LENGTH: 107
<212> TYPE: PRT
<213> ORGANISM: Artificial sequence
<220> FEATURE:
<223> OTHER INFORMATION: Synthetic Light chain variable region

<400> SEQUENCE: 42

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Asn Val Asp Thr Ser
                20                  25                  30

Val Ala Trp Phe Gln Gln Lys Pro Gly Gln Pro Pro Lys Ala Leu Ile
            35                  40                  45

Tyr Ser Ala Ser Phe Arg Tyr Ser Gly Val Pro Asp Arg Phe Ser Gly
        50                  55                  60

Ser Gly Ser Gly Thr Asp Phe Thr Leu Thr Ile Ser Ser Leu Gln Ala
65                  70                  75                  80

Glu Asp Val Ala Val Tyr Phe Cys Gln Gln Tyr Tyr Gly Tyr Pro Phe
                85                  90                  95

Thr Phe Gly Gln Gly Thr Lys Leu Glu Ile Lys
            100                 105

<210> SEQ ID NO 43

<211> LENGTH: 321
<212> TYPE: DNA
<213> ORGANISM: Artificial sequence
<220> FEATURE:
<223> OTHER INFORMATION: Synthetic Nucleotide sequence of the light chain variable region

<400> SEQUENCE: 43

| gacatcgtga tgacccagag ccccgacagc ctggccgtga gcctgggcga gagagccacc | 60 |
| atcaactgca aggccagcca gaacgtggac accagcgtgg cctggttcca gcagaagccc | 120 |
| ggccagcccc ccaaggccct gatctacagc gccagcttca gatacagcgg cgtgcccgac | 180 |
| agattcagcg gcagcggcag cggcaccgac ttcacccctga ccatcagcag cctgcaggcc | 240 |
| gaggacgtgg ccgtgtactt ctgccagcag tactacggct accccttcac cttcggccag | 300 |
| ggcaccaagc tggagatcaa g | 321 |

<210> SEQ ID NO 44
<211> LENGTH: 118
<212> TYPE: PRT
<213> ORGANISM: Artificial sequence
<220> FEATURE:
<223> OTHER INFORMATION: Synthetic Heavy chain variable region

<400> SEQUENCE: 44

```
Gln Gly Gln Leu Gln Glu Ser Gly Pro Ser Leu Val Lys Pro Ser Gln
1               5                   10                  15

Thr Leu Ser Leu Thr Cys Thr Val Ser Gly Asp Ser Ile Thr Arg Gly
            20                  25                  30

Tyr Trp Asn Trp Ile Arg Lys His Pro Gly Lys Gly Leu Glu Tyr Ile
        35                  40                  45

Gly Tyr Ile Ser Tyr Thr Gly Ser Thr Tyr Ser Asn Leu Ser Leu Lys
    50                  55                  60

Ser Arg Val Thr Ile Ser Arg Asp Thr Ser Lys Asn Gln Tyr Tyr Leu
65                  70                  75                  80

Lys Leu Ser Ser Val Thr Ala Ala Asp Thr Ala Val Tyr Tyr Cys Ala
                85                  90                  95

Thr Ser Thr Gly Trp Leu Asp Pro Val Asp Tyr Trp Gly Gln Gly Thr
            100                 105                 110

Leu Val Thr Val Ser Ser
        115
```

<210> SEQ ID NO 45
<211> LENGTH: 354
<212> TYPE: DNA
<213> ORGANISM: Artificial sequence
<220> FEATURE:
<223> OTHER INFORMATION: Synthetic Nucleotide sequence of the heavy chain variable region

<400> SEQUENCE: 45

| cagggccagc tgcaggagag cggccccagc ctggtgaagc ccagccagac cctgagcctg | 60 |
| acctgcaccg tgagcggcga cagcatcacc agaggctact ggaactggat cagaaagcac | 120 |
| cccggcaagg gcctggagta catcggctac atcagctaca ccggcagcac ctacagcaac | 180 |
| ctgagcctga agtccagagt gaccatcagc agagacacca gcaagaacca gtactacctg | 240 |
| aagctgagca gcgtgaccgc cgccgacacc gccgtgtact actgcgccac cagcaccggc | 300 |
| tggctggacc ccgtggacta ctggggccag ggcaccctgg tgaccgtgag cagc | 354 |

<210> SEQ ID NO 46
<211> LENGTH: 107
<212> TYPE: PRT
<213> ORGANISM: Artificial sequence
<220> FEATURE:
<223> OTHER INFORMATION: Synthetic Light chain variable region

<400> SEQUENCE: 46

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Val Asp Thr Ser
            20                  25                  30

Val Ala Trp Phe Gln Gln Lys Pro Gly Lys Ala Pro Lys Ala Leu Ile
        35                  40                  45

Tyr Ser Ala Ser Phe Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Tyr Gly Tyr Pro Phe
                85                  90                  95

Thr Phe Gly Gln Gly Thr Lys Leu Glu Ile Lys
            100                 105
```

<210> SEQ ID NO 47
<211> LENGTH: 321
<212> TYPE: DNA
<213> ORGANISM: Artificial sequence
<220> FEATURE:
<223> OTHER INFORMATION: Synthetic Nucleotide sequence of the light
      chain variable region

<400> SEQUENCE: 47

```
gacatccaga tgacccagag ccccagcagc ctgagcgcca gcgtgggcga cagagtgacc      60
atcacctgca gagccagcca gaacgtggac accagcgtgg cctggttcca gcagaagccc     120
ggcaaggccc ccaaggccct gatctacagc gccagcttca gatacagcgg cgtgcccagc     180
agattcagcg gcagcggcag cggcaccgac ttcaccctga ccatcagcag cctgcagccc     240
gaggacttcg ccacctactt ctgccagcag tactacggct accccttcac cttcggccag     300
ggcaccaagc tggagatcaa g                                               321
```

<210> SEQ ID NO 48
<211> LENGTH: 118
<212> TYPE: PRT
<213> ORGANISM: Artificial sequence
<220> FEATURE:
<223> OTHER INFORMATION: Synthetic Heavy chain variable region

<400> SEQUENCE: 48

```
Gln Gly Gln Leu Gln Glu Ser Gly Pro Ser Leu Val Lys Pro Ser Gln
1               5                   10                  15

Thr Leu Ser Leu Thr Cys Thr Val Ser Gly Asp Ser Ile Thr Arg Gly
            20                  25                  30

Tyr Trp Asn Trp Ile Arg Lys Pro Pro Gly Lys Gly Leu Glu Tyr Ile
        35                  40                  45

Gly Tyr Ile Ser Tyr Thr Gly Ser Thr Tyr Ser Asn Leu Ser Leu Lys
    50                  55                  60

Ser Arg Val Thr Ile Ser Arg Asp Thr Ser Lys Asn Gln Tyr Tyr Leu
65                  70                  75                  80

Lys Leu Ser Ser Val Thr Ala Ala Asp Thr Ala Val Tyr Tyr Cys Ala
```

```
                      85                  90                  95
Thr Ser Thr Gly Trp Leu Asp Pro Val Asp Tyr Trp Gly Gln Gly Thr
            100                 105                 110
Leu Val Thr Val Ser Ser
        115

<210> SEQ ID NO 49
<211> LENGTH: 354
<212> TYPE: DNA
<213> ORGANISM: Artificial sequence
<220> FEATURE:
<223> OTHER INFORMATION: Synthetic Nucleotide sequence of the heavy
      chain variable region

<400> SEQUENCE: 49
cagggccagc tgcaggagag cggcccagc ctggtgaagc ccagccagac cctgagcctg      60
acctgcaccg tgagcggcga cagcatcacc agaggctact ggaactggat cagaaagccc    120
cccggcaagg gcctggagta catcggctac atcagctaca ccggcagcac ctacagcaac    180
ctgagcctga agtccagagt gaccatcagc agagacacca gcaagaacca gtactacctg    240
aagctgagca gcgtgaccgc cgccgacacc gccgtgtact actgcgccac cagcaccggc    300
tggctggacc ccgtggacta ctggggccag ggcaccctgg tgaccgtgag cagc          354

<210> SEQ ID NO 50
<211> LENGTH: 32
<212> TYPE: DNA
<213> ORGANISM: Artificial sequence
<220> FEATURE:
<223> OTHER INFORMATION: Synthetic primer

<400> SEQUENCE: 50
gtacgctagc caccatgagg atatttgctg tc                                   32

<210> SEQ ID NO 51
<211> LENGTH: 29
<212> TYPE: DNA
<213> ORGANISM: Artificial sequence
<220> FEATURE:
<223> OTHER INFORMATION: Synthetic primer

<400> SEQUENCE: 51
gatcctcgag cgtgagtcct ttcatttgg                                       29
```